US010365269B2

(12) United States Patent
Melancon et al.

(10) Patent No.: US 10,365,269 B2
(45) Date of Patent: Jul. 30, 2019

(54) SYSTEM AND METHODS FOR DETECTING RIBOSOME INHIBITION

(71) Applicants: STC.UNM, Albuquerque, NM (US); Charles Melancon, Albuquerque, NM (US); Shijie Huang, Albuquerque, NM (US)

(72) Inventors: Charles Melancon, Albuquerque, NM (US); Shijie Huang, Albuquerque, NM (US)

(*) Notice: Subject to any disclaimer, the term of this patent is extended or adjusted under 35 U.S.C. 154(b) by 0 days.

(21) Appl. No.: 15/577,809

(22) PCT Filed: Jun. 2, 2016

(86) PCT No.: PCT/US2016/035451
§ 371 (c)(1),
(2) Date: Nov. 29, 2017

(87) PCT Pub. No.: WO2016/196749
PCT Pub. Date: Dec. 8, 2016

(65) Prior Publication Data
US 2018/0156783 A1 Jun. 7, 2018

Related U.S. Application Data

(60) Provisional application No. 62/169,637, filed on Jun. 2, 2015.

(51) Int. Cl.
| | |
|---|---|
| *G01N 33/50* | (2006.01) |
| *C12Q 1/68* | (2018.01) |
| *G01N 33/53* | (2006.01) |
| *C12Q 1/6897* | (2018.01) |
| *G01N 33/533* | (2006.01) |

(52) U.S. Cl.
CPC ....... *G01N 33/5076* (2013.01); *C12Q 1/6897* (2013.01); *G01N 33/533* (2013.01)

(58) Field of Classification Search
None
See application file for complete search history.

(56) References Cited

U.S. PATENT DOCUMENTS

| | | | | |
|---|---|---|---|---|
| 2007/0117107 A1* | 5/2007 | Cunningham | ..... | C12N 15/1058 435/5 |
| 2017/0073381 A1* | 3/2017 | Jewett | ..... | C12N 15/67 |

OTHER PUBLICATIONS

Beck et al. "A Mulitfunctional Gene (tetR) Controls Tn10-Encoded Tetracycline Resistance," *J. of Bacteriology*, May 1982; 50(2):633-642.
Brosius et al. "Construction and Fine Mapping of Recombinant Plasmids Containing the rrnB Ribosomal RNA Operon of *E. coli*," *Plasmid*, Feb. 1981; 6:112-118.
Chen et al. "Characterization of 582 Natural and Synthetic Terminators and Quantification of Their Design Constraints," *Nature Methods*, Jul. 2013; 10(7):659-664.
Crameri et al. "Improved Green Fluorescent Protein by Molecular Evolution Using DNA Shuffling," *Nature Biotechnology*, Mar. 1996; 14:315-318.
Huang et al. "Direct Detection of Ribosome Inhibition by Aminoglycoside Antibiotics in Living Bacteria Using an Orthogonal Ribosome-Controlled Fluorescent Reporter," *Wiley-VCH*.
Inouye et al. "Up-Promoter Mutations in the lpp Gene of *Escherichia coli*," *Nucleic Acid Research*, Apr. 1985; 13(9):3101-3109.
Lutz et al. "Independent and Tight Regulation of Transcriptional Units in *Escherichia coli* via the LacR/O, the TetR/O and AraC/I1-I2 Regulatory Elements," *Nucleic Acids Res.*, Jan. 1997; 25(6):1203-1210.
Melancon et al. "One Plasmid Selection System for the Rapid Evolution of Aminoacyl-tRNA Synthetases," *Bioorg. Med. Chem. Lett.*, 2009; 19:3845-3847.
Mutalik et al. "Quantitative Estimation of Activity and Quality for Collections of Functional Genetic Elements," *Nat. Methods*, Apr. 2013; 10(4):347-353.
Mutalik et al. "Precise and Reliable Gene Expression via Standard Transcription and Translation Initiation Elements," *Nat. Methods*, Apr. 2013; 10(4): 354-360.
Quan et al. "Circular Polymerase Extension Cloning or High-Throughput Cloning of Complex and Combinatorial DNA Libraries," *Nat. Protocols*, Feb. 2011; 6(2):242-251.
Recht et al. "Basis for Prokaryotic Specificity of Action of Aminoglycoside Antibiotics," *EMBO J.*, 1999; 18(11):3133-3136.
Sambrook et al. "Molecular Cloning: A Laboratory Manual," 3rd Edition 2001; Cold Spring Harbor Laboratory Press, Cold Spring Harbor, NY.
Sucheck et al. "Design of Bifunctional Antibiotics that Target Bacterial rRNA and Inhibit Resistance-Causing Enzymes," *J. Am. Chem. Soc.*, 2000; 122:5230-5231.
Young et al. "An Enhanced System for Unnatural Amino Acid Mutagenesis in *E. coli*," *J. Mol. Biol.*, 2010; 395: 361-374.
Zaporojects et al. "Products Transcribed from Rearranged rrn Genes of *Escherichia coli* Can Assemble to Form Functional Ribosomes," *Bacteriology*, 2003; 185(23): 6921-6927.
Abdi et al. "Contribution of 16S rRNA Nucleotides Forming the 30S Subunit A and P Sites to Translation in *Escherichia coli*," *RNA J.*, 2005; 11:1624-1632.

(Continued)

*Primary Examiner* — Nancy A Treptow
(74) *Attorney, Agent, or Firm* — Mueting, Raasch & Gebhardt, P.A.

(57) ABSTRACT

This disclosure describes a cell genetically modified to detect ribosome inhibition in the cell and methods involving such a cell. Generally, the genetically-modified cell includes an aminoglycoside-sensitive orthogonal 16S rRNA (O-16S) coding region bearing a mutated anti-Shine-Dalgarno (O-ASD) sequence, a repressor/operator system, and a polynucleotide encoding a detectable reporter under transcriptional control of the repressor/operator system. The repressor/operator system includes a coding region that encodes a transcriptional regulator and having an orthogonal SD (O-SD) sequence complementary to the 16S rRNA O-ASD sequence. The operator sequence, which is repressable by the transcriptional regulator, is operably linked to the polynucleotide encoding a detectable reporter.

4 Claims, 21 Drawing Sheets
Specification includes a Sequence Listing.

(56) References Cited

OTHER PUBLICATIONS

Chubiz, L. and Rao, C., "Computational design of orthogonal ribosomes," *Nucleic Acids Res*, 2008; 36(12):4038-4046.
Hui, A. and de Boer, H. "Specialized ribosome system: Preferential translation of a single mRNA species by a subpopulation of mutated ribosomes in *Escherichia coli*," *Proc Natl Acad Sci USA*, 1987; 84:4762-4766.
Lee et al. "Genetic Analysis of the Shine-Dalgarno Interaction: Selection of Alternative Functional mRNA-rRNA Combinations", *RNA J.*, 1996; 2:1270-1285.
Rackham, O. and Chin, J, "A network of orthogonal ribosome•mRNA pairs," *Nature Chemical Biol*, 2005; 1(3):159-166.

* cited by examiner

A

B

SEQUENCE LISTING

```
<160> NUMBER OF SEQ ID NOS: 88

<210> SEQ ID NO 1
<211> LENGTH: 22
<212> TYPE: DNA
<213> ORGANISM: artificial
<220> FEATURE:
<223> OTHER INFORMATION: Primer

<400> SEQUENCE: 1
tttggttgaa tgttgcgcgg tc                                              22

<210> SEQ ID NO 2
<211> LENGTH: 21
<212> TYPE: DNA
<213> ORGANISM: artificial
<220> FEATURE:
<223> OTHER INFORMATION: Primer

<400> SEQUENCE: 2
cggtgtcctg ggcctctaga c                                               21

<210> SEQ ID NO 3
<211> LENGTH: 40
<212> TYPE: DNA
<213> ORGANISM: artificial
<220> FEATURE:
<223> OTHER INFORMATION: Primer

<400> SEQUENCE: 3
tctagaggcc caggacaccg ccctttcacg gcggtaacag                           40

<210> SEQ ID NO 4
<211> LENGTH: 41
<212> TYPE: DNA
<213> ORGANISM: artificial
<220> FEATURE:
<223> OTHER INFORMATION: Primer

<400> SEQUENCE: 4
```

```
ctggtatctt cgactgattt cagctccatc cgcgagggac c                41
```

<210> SEQ ID NO 5
<211> LENGTH: 29
<212> TYPE: DNA
<213> ORGANISM: artificial
<220> FEATURE:
<223> OTHER INFORMATION: Primer

<400> SEQUENCE: 5

```
gctgaaatca gtcgaagata ccagctggc                              29
```

<210> SEQ ID NO 6
<211> LENGTH: 24
<212> TYPE: DNA
<213> ORGANISM: artificial
<220> FEATURE:
<223> OTHER INFORMATION: Primer

<400> SEQUENCE: 6

```
agctgctttc ctgatgcaaa aacg                                   24
```

<210> SEQ ID NO 7
<211> LENGTH: 51
<212> TYPE: DNA
<213> ORGANISM: artificial
<220> FEATURE:
<223> OTHER INFORMATION: Primer

<400> SEQUENCE: 7

```
cgttttgca tcaggaaagc agctgatatc agacgtcagg tggcactttt c       51
```

<210> SEQ ID NO 8
<211> LENGTH: 45
<212> TYPE: DNA
<213> ORGANISM: artificial
<220> FEATURE:
<223> OTHER INFORMATION: Primer

<400> SEQUENCE: 8

```
catatgatca atctaaagta tatatgagta aacttggtct gacag             45
```

<210> SEQ ID NO 9
<211> LENGTH: 58
<212> TYPE: DNA
<213> ORGANISM: artificial
<220> FEATURE:
<223> OTHER INFORMATION: Primer

<400> SEQUENCE: 9

```
ccaagtttac tcatatatac tttagattga tcatatgctt cggatccctc gagagatc   58
```

<210> SEQ ID NO 10
<211> LENGTH: 40
<212> TYPE: DNA
<213> ORGANISM: artificial
<220> FEATURE:
<223> OTHER INFORMATION: Primer

<400> SEQUENCE: 10

```
ccgcgcaaca ttcaaccaaa attacatgtg cgtcagaccc                   40
```

<210> SEQ ID NO 11
<211> LENGTH: 877
<212> TYPE: DNA

<213> ORGANISM: artificial
<220> FEATURE:
<223> OTHER INFORMATION: p15A origin of replication fragment

<400> SEQUENCE: 11

```
attacatgtg cgtcagaccc cttaataaga tgatcttctt gagatcgttt tggtctgcgc    60
gtaatctctt gctctgaaaa cgaaaaaacc gccttgcagg gcggttttc gaaggttctc    120
tgagctacca actctttgaa ccgaggtaac tggcttggag gagcgcagtc accaaaactt    180
gtcctttcag tttagcctta accggcgcat gacttcaaga ctaactcctc taaatcaatt    240
accagtggct gctgccagtg gtgcttttgc atgtctttcc gggttggact caagacgata    300
gttaccggat aaggcgcagc ggtcggactg aacgggggt tcgtgcatac agtccagctt    360
ggagcgaact gcctacccgg aactgagtgt caggcgtgga attagacaaa cgcggccata    420
acagcggaat gacaccggta aaccgaaagg caggaacagg agagcgcacg agggagccgc    480
cagggggaaa cgcctggtat ctttatagtc ctgtcgggtt cgccaccac tgatttgagc    540
gtcagatttc gtgatgcttg tcagggggc ggagcctatg gaaaaacggc tttgccgcgg    600
ccctctcact tccctgttaa gtatcttcct ggcatcttcc aggaaatctc cgccccgttc    660
gtaagccatt tccgctcgcc gcagtcgaac gaccgagcgt agcgagtcag tgagcgagga    720
agcggaatat atcctgtatc acatattctg ctgacgcacc ggtgcagcct ttttctcct    780
gccacatgaa gcacttcact gacaccctca tcagtgccaa catagtaagc cagtatacac    840
tccgctagcc catggagatc tctcgaggga tccgaag                            877
```

<210> SEQ ID NO 12
<211> LENGTH: 24
<212> TYPE: DNA
<213> ORGANISM: artificial
<220> FEATURE:
<223> OTHER INFORMATION: Primer

<400> SEQUENCE: 12

```
tctcaaacat cacccgaaga tgag                                           24
```

<210> SEQ ID NO 13
<211> LENGTH: 20
<212> TYPE: DNA
<213> ORGANISM: artificial
<220> FEATURE:
<223> OTHER INFORMATION: Primer

<400> SEQUENCE: 13

```
cccgtcgcac catgggagtg                                                20
```

<210> SEQ ID NO 14
<211> LENGTH: 22
<212> TYPE: DNA
<213> ORGANISM: artificial
<220> FEATURE:
<223> OTHER INFORMATION: Primer

<400> SEQUENCE: 14

```
ccatggtgcg acgggcggtg tg                                             22
```

<210> SEQ ID NO 15
<211> LENGTH: 21
<212> TYPE: DNA
<213> ORGANISM: artificial
<220> FEATURE:
<223> OTHER INFORMATION: Primer

```
<400> SEQUENCE: 15
gaggaaggtg gggatgacgt c                                              21

<210> SEQ ID NO 16
<211> LENGTH: 20
<212> TYPE: DNA
<213> ORGANISM: artificial
<220> FEATURE:
<223> OTHER INFORMATION: Primer

<400> SEQUENCE: 16
cccgacacac catgggagtg                                                20

<210> SEQ ID NO 17
<211> LENGTH: 24
<212> TYPE: DNA
<213> ORGANISM: artificial
<220> FEATURE:
<223> OTHER INFORMATION: Primer

<400> SEQUENCE: 17
actcccatgg tgtgtcgggc ggtg                                           24

<210> SEQ ID NO 18
<211> LENGTH: 41
<212> TYPE: DNA
<213> ORGANISM: artificial
<220> FEATURE:
<223> OTHER INFORMATION: Primer

<400> SEQUENCE: 18
acaaactagt gcgaccctgc gtatcacgag gccctttcgt c                        41

<210> SEQ ID NO 19
<211> LENGTH: 54
<212> TYPE: DNA
<213> ORGANISM: artificial
<220> FEATURE:
<223> OTHER INFORMATION: Primer

<400> SEQUENCE: 19
catggtgaag ggctcctgaa ttccttcatt aatggtcagt gcgtcctgct gatg          54

<210> SEQ ID NO 20
<211> LENGTH: 27
<212> TYPE: DNA
<213> ORGANISM: artificial
<220> FEATURE:
<223> OTHER INFORMATION: Primer

<400> SEQUENCE: 20
gaaggaattc aggagccctt caccatg                                        27

<210> SEQ ID NO 21
<211> LENGTH: 21
<212> TYPE: DNA
<213> ORGANISM: artificial
<220> FEATURE:
<223> OTHER INFORMATION: Primer

<400> SEQUENCE: 21
ccgggcctct tgcgggatat c                                              21

<210> SEQ ID NO 22
```

<211> LENGTH: 55
<212> TYPE: DNA
<213> ORGANISM: artificial
<220> FEATURE:
<223> OTHER INFORMATION: Primer

<400> SEQUENCE: 22
atatcccgca agaggcccgg gcggtaataa gcttacggtt atccacagaa tcagg    55

<210> SEQ ID NO 23
<211> LENGTH: 41
<212> TYPE: DNA
<213> ORGANISM: artificial
<220> FEATURE:
<223> OTHER INFORMATION: Primer

<400> SEQUENCE: 23
agaccccgtc tagatagaaa agatcaaagg atcttcttga g    41

<210> SEQ ID NO 24
<211> LENGTH: 40
<212> TYPE: DNA
<213> ORGANISM: artificial
<220> FEATURE:
<223> OTHER INFORMATION: Primer

<400> SEQUENCE: 24
ctttgatctt ttctatctag acggggtctg acgctcagtg    40

<210> SEQ ID NO 25
<211> LENGTH: 56
<212> TYPE: DNA
<213> ORGANISM: artificial
<220> FEATURE:
<223> OTHER INFORMATION: Primer

<400> SEQUENCE: 25
gcagggtcgc actagtttgt ttatttttct aaatacattc aaatatgtat ccgctc    56

<210> SEQ ID NO 26
<211> LENGTH: 1022
<212> TYPE: DNA
<213> ORGANISM: artificial
<220> FEATURE:
<223> OTHER INFORMATION: gfp-uv fragment

<400> SEQUENCE: 26
gaaggaattc aggagccctt caccatgagt aaaggagaag aacttttcac tggagttgtc    60
ccaattcttg ttgaattaga tggtgatgtt aatgggcaca attttctgt cagtggagag    120
ggtgaaggtg atgcaacata cggaaaactt acccttaaat ttatttgcac tactggaaaa    180
ctacctgttc catggccaac acttgtcact actttctctt atggtgttca atgcttttcc    240
cgttatccgg atcacatgaa acggcatgac ttttcaaga gtgccatgcc cgaaggttat    300
gtacaggaac gcactatatc tttcaaagat gacgggaact acaagacgcg tgctgaagtc    360
aagtttgaag gtgataccct tgttaatcgt atcgagttaa aggtattga ttttaaagaa    420
gatggaaaca ttctcggaca caaactcgaa tacaactata actcacacaa tgtatacatc    480
acggcagaca aacaaaagaa tggaatcaaa gctaacttca aaattcgcca acacattgaa    540
gatggatccg ttcaactagc agaccattat caacaaaata ctccaattgg cgatggccct    600
gtccttttac cagacaacca ttacctgtcg acacaatctg cccttttcgaa agatcccaac    660
gaaaagcgtg accacatggt ccttcttgag tttgtaactg ctgctgggat tacacatggc    720

```
atggatgagc tctacaaact cgagcaccac caccaccacc actgaaaggg cgagctcaat    780
tcgaagcttg aaggtaagcc tatccctaac cctctcctcg gtctcgattc tacgcgtacc    840
ggtcatcatc accatcacca ttgagtttga tccggctgct aacaaagccc gaaaggaagc    900
tgagttggct gctgccaccg ctgagcaata actagcataa ccccttgggg cctctaaacg    960
ggtcttgagg ggttttttgc tgaaaggagg aactatatcc ggatatcccg caagaggccc   1020
gg                                                                  1022
```

<210> SEQ ID NO 27
<211> LENGTH: 46
<212> TYPE: DNA
<213> ORGANISM: artificial
<220> FEATURE:
<223> OTHER INFORMATION: Primer

<400> SEQUENCE: 27

```
acaaactagt gcgaccctgc tgcttggatt ctcaccaata aaaaac                    46
```

<210> SEQ ID NO 28
<211> LENGTH: 60
<212> TYPE: DNA
<213> ORGANISM: artificial
<220> FEATURE:
<223> OTHER INFORMATION: Primer

<400> SEQUENCE: 28

```
tgtcaatctc tatcactgat agggatttga tatcgagctc gcttggactc ctgttgatag    60
```

<210> SEQ ID NO 29
<211> LENGTH: 56
<212> TYPE: DNA
<213> ORGANISM: artificial
<220> FEATURE:
<223> OTHER INFORMATION: Primer

<400> SEQUENCE: 29

```
gctcagtatc tctatcactg atagggatgt caatctctat cactgatagg gatttg        56
```

<210> SEQ ID NO 30
<211> LENGTH: 48
<212> TYPE: DNA
<213> ORGANISM: artificial
<220> FEATURE:
<223> OTHER INFORMATION: Primer

<400> SEQUENCE: 30

```
ggtcagtgcg tcctgctgat gtgctcagta tctctatcac tgatagggg                 48
```

<210> SEQ ID NO 31
<211> LENGTH: 59
<212> TYPE: DNA
<213> ORGANISM: artificial
<220> FEATURE:
<223> OTHER INFORMATION: Primer

<400> SEQUENCE: 31

```
atcagcagga cgcactgacc cctctagaaa taattttgtt taactttaag aaggaattc     59
```

<210> SEQ ID NO 32
<211> LENGTH: 21
<212> TYPE: DNA
<213> ORGANISM: artificial
<220> FEATURE:

<223> OTHER INFORMATION: Primer

<400> SEQUENCE: 32
ccgggcctct tgcgggatat c                                      21

<210> SEQ ID NO 33
<211> LENGTH: 47
<212> TYPE: DNA
<213> ORGANISM: artificial
<220> FEATURE:
<223> OTHER INFORMATION: Primer

<400> SEQUENCE: 33
aaagaggaga aaggtaccat gagtaaagga gaagaacttt tcactgg           47

<210> SEQ ID NO 34
<211> LENGTH: 52
<212> TYPE: DNA
<213> ORGANISM: artificial
<220> FEATURE:
<223> OTHER INFORMATION: Primer

<400> SEQUENCE: 34
atcagcagga cgcactgacc gaattcatta aagaggagaa aggtaccatg ag     52

<210> SEQ ID NO 35
<211> LENGTH: 51
<212> TYPE: DNA
<213> ORGANISM: artificial
<220> FEATURE:
<223> OTHER INFORMATION: Primer

<400> SEQUENCE: 35
agcaaagccc aatttttaaac aaatgagtaa aggagaagaa cttttcactg g     51

<210> SEQ ID NO 36
<211> LENGTH: 53
<212> TYPE: DNA
<213> ORGANISM: artificial
<220> FEATURE:
<223> OTHER INFORMATION: Primer

<400> SEQUENCE: 36
atcagcagga cgcactgacc gcataaagga cttagcaaag cccaatttta aac    53

<210> SEQ ID NO 37
<211> LENGTH: 55
<212> TYPE: DNA
<213> ORGANISM: artificial
<220> FEATURE:
<223> OTHER INFORMATION: Primer

<400> SEQUENCE: 37
attttgttta actttaagaa ggatccatga gtaaaggaga agaacttttc actgg  55

<210> SEQ ID NO 38
<211> LENGTH: 59
<212> TYPE: DNA
<213> ORGANISM: artificial
<220> FEATURE:
<223> OTHER INFORMATION: Primer

<400> SEQUENCE: 38
atcagcagga cgcactgacc gctagcaata attttgttta actttaagaa ggatccatg   59

```
<210> SEQ ID NO 39
<211> LENGTH: 51
<212> TYPE: DNA
<213> ORGANISM: artificial
<220> FEATURE:
<223> OTHER INFORMATION: Primer

<400> SEQUENCE: 39
atcagcagga cgcactgacc gggcccaagt tcacttaaaa aggagatcaa c            51

<210> SEQ ID NO 40
<211> LENGTH: 53
<212> TYPE: DNA
<213> ORGANISM: artificial
<220> FEATURE:
<223> OTHER INFORMATION: Primer

<400> SEQUENCE: 40
gattaagatg tttcagtacg aaaattgctt tcattgttga tctccttttt aag          53

<210> SEQ ID NO 41
<211> LENGTH: 58
<212> TYPE: DNA
<213> ORGANISM: artificial
<220> FEATURE:
<223> OTHER INFORMATION: Primer

<400> SEQUENCE: 41
agttcttctc ctttactcat tagaaaacct ccttagcatg attaagatgt ttcagtac     58

<210> SEQ ID NO 42
<211> LENGTH: 31
<212> TYPE: DNA
<213> ORGANISM: artificial
<220> FEATURE:
<223> OTHER INFORMATION: Primer

<400> SEQUENCE: 42
atgagtaaag gagaagaact tttcactgga g                                  31

<210> SEQ ID NO 43
<211> LENGTH: 123
<212> TYPE: DNA
<213> ORGANISM: artificial
<220> FEATURE:
<223> OTHER INFORMATION: T0 spacer fragment

<400> SEQUENCE: 43
tgcttggatt ctcaccaata aaaaacgccc ggcggcaacc gagcgttctg aacaaatcca   60
gatggagttc tgaggtcatt actggatcta tcaacaggag tccaagcgag ctcgatatca  120
aat                                                                123

<210> SEQ ID NO 44
<211> LENGTH: 53
<212> TYPE: DNA
<213> ORGANISM: artificial
<220> FEATURE:
<223> OTHER INFORMATION: pET 5'-UTR

<400> SEQUENCE: 44
cctctagaaa taattttgtt taactttaag aaggaattca ggagcccttc acc           53

<210> SEQ ID NO 45
<211> LENGTH: 27
<212> TYPE: DNA
```

<213> ORGANISM: artificial
<220> FEATURE:
<223> OTHER INFORMATION: U2 5'-UTR

<400> SEQUENCE: 45
gaattcatta aagaggagaa aggtacc                                           27

<210> SEQ ID NO 46
<211> LENGTH: 35
<212> TYPE: DNA
<213> ORGANISM: artificial
<220> FEATURE:
<223> OTHER INFORMATION: 26_2 5'-UTR

<400> SEQUENCE: 46
gcataaagga cttagcaaag cccaatttta aacaa                                  35

<210> SEQ ID NO 47
<211> LENGTH: 36
<212> TYPE: DNA
<213> ORGANISM: artificial
<220> FEATURE:
<223> OTHER INFORMATION: pBEST 5'-UTR

<400> SEQUENCE: 47
gctagcaata attttgttta actttaagaa ggatcc                                 36

<210> SEQ ID NO 48
<211> LENGTH: 85
<212> TYPE: DNA
<213> ORGANISM: artificial
<220> FEATURE:
<223> OTHER INFORMATION: BCD2 5'-UTR

<400> SEQUENCE: 48
gggcccaagt tcacttaaaa aggagatcaa caatgaaagc aatttccgta ctgaaacatc       60
ttaatcatgc taaggaggtt ttcta                                             85

<210> SEQ ID NO 49
<211> LENGTH: 50
<212> TYPE: DNA
<213> ORGANISM: artificial
<220> FEATURE:
<223> OTHER INFORMATION: Primer

<400> SEQUENCE: 49
cttttctatc tagacggggt cttttgatag aaaatcataa aaggatttgc                  50

<210> SEQ ID NO 50
<211> LENGTH: 50
<212> TYPE: DNA
<213> ORGANISM: artificial
<220> FEATURE:
<223> OTHER INFORMATION: Primer

<400> SEQUENCE: 50
gcagggtcgc actagtttgt ggatccaact gcattcagaa taaataaatc                  50

<210> SEQ ID NO 51
<211> LENGTH: 1027
<212> TYPE: DNA
<213> ORGANISM: artificial
<220> FEATURE:
<223> OTHER INFORMATION: chloramphenicol resistance marker fragment

<400> SEQUENCE: 51

```
ggatccaact gcattcagaa taaataaatc ctggtgtccc tgttgatacc gggaagccct    60
gggccaactt ttggcgaaaa tgagacgttg atcggcacgt aagaggttcc aactttcacc   120
ataatgaaat aagatcacta ccgggcgtat tttttgagtt gtcgagattt tcaggagcta   180
aggaagctaa aatggagaaa aaaatcactg gatataccac cgttgatata tcccaatggc   240
atcgtaaaga acattttgag gcatttcagt cagttgctca atgtacctat aaccagaccg   300
ttcagctgga tattacggcc ttttaaaga ccgtaaagaa aaataagcac aagttttatc   360
cggcctttat tcacattctt gcccgcctga tgaatgctca tccggaatta cgtatggcaa   420
tgaaagacgg tgagctggtg atatgggata gtgttcaccc ttgttacacc gttttccatg   480
agcaaactga aacgttttca tcgctctgga gtgaatacca cgacgatttc cggcagtttc   540
tacacatata ttcgcaagat gtggcgtgtt acggtgaaaa cctggcctat ttccctaaag   600
ggtttattga gaatatgttt ttcgtctcag ccaatccctg ggtgagtttc accagttttg   660
atttaaacgt ggccaatatg gacaacttct tcgcccccgt tttccaccatg gcaaatatt   720 atacgcaagg cgacaaggtg ctgatgccgc tggcgattca ggttcatcat gccgtttgtg   780
atggcttcca tgtcggcaga atgcttaatg aattacaaca gtactgcgat gagtggcagg   840
gcggggcgta aggcgcgcca tttaaatgaa gttcctattc cgaagttcct attcctaggg   900
attaaaaagg caactttatg cccatgcaac agaaactata aaaatacag agaatgaaaa   960 gaaacagata gattttttag ttctttaggc ccgtagtctg caaatccttt tatgattttc  1020
tatcaaa                                                            1027
```

<210> SEQ ID NO 52
<211> LENGTH: 26
<212> TYPE: DNA
<213> ORGANISM: artificial
<220> FEATURE:
<223> OTHER INFORMATION: Primer

<400> SEQUENCE: 52
gcggtaataa gcttacggtt atccac                                         26

<210> SEQ ID NO 53
<211> LENGTH: 41
<212> TYPE: DNA
<213> ORGANISM: artificial
<220> FEATURE:
<223> OTHER INFORMATION: Primer

<400> SEQUENCE: 53
agaccccgtc tagatagaaa agatcaaagg atcttcttga g                        41

<210> SEQ ID NO 54
<211> LENGTH: 50
<212> TYPE: DNA
<213> ORGANISM: artificial
<220> FEATURE:
<223> OTHER INFORMATION: Primer

<400> SEQUENCE: 54
acaatcgata catcccccgc aaatgatgtc tcgtttagat aaaagtaaag                50

<210> SEQ ID NO 55
<211> LENGTH: 47
<212> TYPE: DNA
<213> ORGANISM: artificial
<220> FEATURE:

<223> OTHER INFORMATION: Primer

<400> SEQUENCE: 55
tgtggataac cgtaagctta ttaccgcttt gagtgagctg ataccgc      47

<210> SEQ ID NO 56
<211> LENGTH: 58
<212> TYPE: DNA
<213> ORGANISM: artificial
<220> FEATURE:
<223> OTHER INFORMATION: Primer

<400> SEQUENCE: 56
ctagctcagt cctaggtata gtgctagccc agccagagaa acaatcgata catccccc      58

<210> SEQ ID NO 57
<211> LENGTH: 42
<212> TYPE: DNA
<213> ORGANISM: artificial
<220> FEATURE:
<223> OTHER INFORMATION: Primer

<400> SEQUENCE: 57
atatcccgca agaggcccgg tttacggcta gctcagtcct ag      42

<210> SEQ ID NO 58
<211> LENGTH: 775
<212> TYPE: DNA
<213> ORGANISM: artificial
<220> FEATURE:
<223> OTHER INFORMATION: tetR-T1 terminator fragment

<400> SEQUENCE: 58
atgatgtctc gtttagataa aagtaaagtg attaacagcg cattagagct gcttaatgag      60
gtcggaatcg aaggtttaac aacccgtaaa ctcgcccaga agctaggtgt agagcagcct     120
acattgtatt ggcatgtaaa aaataagcgg gctttgctcg acgccttagc cattgagatg     180
ttagataggc accatactca cttttgccct ttagaagggg aaagctggca agattttttta   240
cgtaataacg ctaaaagttt tagatgtgct ttactaagtc atcgcgatgg agcaaaagta     300
catttaggta cacggcctac agaaaaacag tatgaaactc tcgaaaatca attagccttt     360
ttatgccaac aaggttttt c actagagaat gcattatatg cactcagcgc agtgggcat    420
tttactttag gttgcgtatt ggaagatcaa gagcatcaag tcgctaaaga agaaagggaa     480
acacctacta ctgatagtat gccgccatta ttacgacaag ctatcgaatt atttgatcac    540
caaggtgcag agccagcctt cttattcggc cttgaattga tcatatgcgg attagaaaaa    600
caacttaaat gtgaaagtgg gtcttaaggc atcaaataaa acgaaaggct cagtcgaaag    660
actgggcctt tcgttttatc tgttgtttgt cggtgaacgc tctcctgagt aggacaaatc    720
cgccgcccta gacctaggcg ttcggctgcg gcgagcggta tcagctcact caaag         775

<210> SEQ ID NO 59
<211> LENGTH: 615
<212> TYPE: DNA
<213> ORGANISM: artificial
<220> FEATURE:
<223> OTHER INFORMATION: pMB1 origin

<400> SEQUENCE: 59
cgcgttgctg gcgttttttcc ataggctccg ccccccctgac gagcatcaca aaaatcgacg    60
ctcaagtcag aggtggcgaa acccgacagg actataaaga taccagccgt ttccccctgg   120

-continued

```
aagctccctc gtgcgctctc ctgttccgac cctgccgctt accggatacc tgtccgcctt      180
tctcccttcg ggaagcgtgg cgctttctca tagctcacgc tgtaggtatc tcagttcggt      240
gtaggtcgtt cgctccaagc tgggctgtgt gcacgaaccc cccgttcagc ccgaccgctg      300
cgccttatcc ggtaactatc gtcttgagtc caacccggta agacacgact tatcgccact      360
ggcagcagcc actggtaaca ggattagcag agcgaggtat gtaggcggtg ctacagagtt      420
cttgaagtgg tggcctaact acggctacac tagaagaaca gtatttggta tctgcgctct      480
gctgaagcca gttaccttcg gaaaaagagt tggtagctct tgatccggca aacaaaccac      540
cgctggtagc ggtggttttt ttgtttgcaa gcagcagatt acgcgcagaa aaaaggatc      600 tcaagaagat cctttt                                                      615
```

<210> SEQ ID NO 60
<211> LENGTH: 43
<212> TYPE: DNA
<213> ORGANISM: artificial
<220> FEATURE:
<223> OTHER INFORMATION: Primer
<400> SEQUENCE: 60

```
gaattcgtgg ccctgcatgc acaaactagt gcgaccctgc tgc                         43
```

<210> SEQ ID NO 61
<211> LENGTH: 21
<212> TYPE: DNA
<213> ORGANISM: artificial
<220> FEATURE:
<223> OTHER INFORMATION: Primer
<400> SEQUENCE: 61

```
ccgggcctct tgcgggatat c                                                 21
```

<210> SEQ ID NO 62
<211> LENGTH: 50
<212> TYPE: DNA
<213> ORGANISM: artificial
<220> FEATURE:
<223> OTHER INFORMATION: Primer
<400> SEQUENCE: 62

```
cttttctatc tagacggggt cttttgatag aaaatcataa aaggatttgc                  50
```

<210> SEQ ID NO 63
<211> LENGTH: 50
<212> TYPE: DNA
<213> ORGANISM: artificial
<220> FEATURE:
<223> OTHER INFORMATION: Primer
<400> SEQUENCE: 63

```
gtacccgtgg atcctctaga ggatccaact gcattcagaa taaataaatc                  50
```

<210> SEQ ID NO 64
<211> LENGTH: 88
<212> TYPE: DNA
<213> ORGANISM: artificial
<220> FEATURE:
<223> OTHER INFORMATION: Primer
<400> SEQUENCE: 64

```
gcatgcaggg ccacgaattc tcaacataaa aaactttgtg taatacttgt aacgctagat       60
```

```
ccggtagcga tcgaaagcga agcggcac                                          88
```

<210> SEQ ID NO 65
<211> LENGTH: 69
<212> TYPE: DNA
<213> ORGANISM: artificial
<220> FEATURE:
<223> OTHER INFORMATION: Primer

<400> SEQUENCE: 65

```
ctgcagtatc agacaatctg tgtgagcact acaaagtacg cttctttaag gtaccccatg        60
atccaaccg                                                               69
```

<210> SEQ ID NO 66
<211> LENGTH: 43
<212> TYPE: DNA
<213> ORGANISM: artificial
<220> FEATURE:
<223> OTHER INFORMATION: Primer

<400> SEQUENCE: 66

```
cagattgtct gatactgcag gcatgataat aatctagacc agg                         43
```

<210> SEQ ID NO 67
<211> LENGTH: 21
<212> TYPE: DNA
<213> ORGANISM: artificial
<220> FEATURE:
<223> OTHER INFORMATION: Primer

<400> SEQUENCE: 67

```
tctagaggat ccacgggtac c                                                 21
```

<210> SEQ ID NO 68
<211> LENGTH: 1802
<212> TYPE: DNA
<213> ORGANISM: artificial
<220> FEATURE:
<223> OTHER INFORMATION: lpp promoter - O16S fragment

<400> SEQUENCE: 68

```
attctcaaca taaaaaactt tgtgtaatac ttgtaacgct agatccggta gcgatcgaaa        60
gcgaagcggc actgctcttt aacaatttat cagacaatct gtgtgggcac tcgaagatac      120
ggattcttaa cgtcgcaaga cgaaaaatga ataccaagtc tcaagagtga acacgtaatt      180
cattacgaag tttaattctt tgagcgtcaa acttttaaat tgaagagttt gatcatggct      240
cagattgaac gctggcggca ggcctaacac atgcaagtcg aacggtaaca ggaagaagct      300
tgcttctttg ctgacgagtg gcggacgggt gagtaatgtc tgggaaactg cctgatggag      360
ggggataact actggaaacg gtagctaata ccgcataacg tcgcaagacc aaagaggggg      420
accttcgggc ctcttgccat cggatgtgcc cagatgggat tagctagtag gtggggtaac      480
ggctcaccta ggcgacgatc cctagctggt ctgagaggat gaccagccac actggaactg      540
agacacggtc cagactccta cgggaggcag cagtggggaa tattgcacaa tgggcgcaag      600
cctgatgcag ccatgccgcg tgtatgaaga aggccttcgg gttgtaaagt actttcagcg      660
gggaggaagg gagtaaagtt aatacctttg ctcattgacg ttacccgcag aagaagcacc      720
ggctaactcc gtgccagcag ccgcggtaat acgagggtg caagcgttaa tcggaattac      780
tgggcgtaaa gcgcacgcag gcggtttgtt aagtcagatg tgaaatcccc gggctcaacc      840
tgggaactgc atctgatact ggcaagcttg agtctcgtag agggggtag aattccaggt      900
```

```
gtagcggtga aatgcgtaga gatctggagg aataccggtg gcgaaggcgg ccccctggac      960
gaagactgac gctcaggtgc gaaagcgtgg ggagcaaaca ggattagata ccctggtagt     1020
ccacgccgta aacgatgtcg acttggaggt tgtgcccttg aggcgtggct tccggagcta     1080
acgcgttaag tcgaccgcct ggggagtacg gccgcaaggt taaaactcaa atgaattgac     1140
gggggcccgc acaagcggtg gagcatgtgg tttaattcga tgcaacgcga agaaccttac     1200
ctggtcttga catccacgga agttttcaga gatgagaatg tgccttcggg aaccgtgaga     1260
caggtgctgc atggctgtcg tcagctcgtg ttgtgaaatg ttgggttaag tcccgcaacg     1320
agcgcaaccc ttatcctttg ttgccagcgg tccggccggg aactcaaagg agactgccag     1380
tgataaactg gaggaaggtg gggatgacgt caagtcatca tggcccttac gaccagggct     1440
acacacgtgc tacaatggcg catacaaaga gaagcgacct cgcgagagca agcggacctc     1500
ataaagtgcg tcgtagtccg gattggagtc tgcaactcga ctccatgaag tcggaatcgc     1560
tagtaatcgt ggatcagaat gccacggtga atacgttccc gggccttgta cacaccgccc     1620
gtcacaccat gggagtgggt tgcaaaagaa gtaggtagct taaccttcgg gagggcgctt     1680
accactttgt gattcatgac tggggtgaag tcgtaacaag gtaaccgtag ggaacctgc      1740 ggttggatca tggggtacct taagaagcg tactttgtag tgctcacaca gattgtctga      1800
ta                                                                    1802

<210> SEQ ID NO 69
<211> LENGTH: 35
<212> TYPE: DNA
<213> ORGANISM: artificial
<220> FEATURE:
<223> OTHER INFORMATION: promoter

<400> SEQUENCE: 69
ttgacggcta gctcagtcct aggtacagtg ctagc                                35

<210> SEQ ID NO 70
<211> LENGTH: 35
<212> TYPE: DNA
<213> ORGANISM: artificial
<220> FEATURE:
<223> OTHER INFORMATION: promoter

<400> SEQUENCE: 70
tttacggcta gctcagtcct aggtatagtg ctagc                                35

<210> SEQ ID NO 71
<211> LENGTH: 35
<212> TYPE: DNA
<213> ORGANISM: artificial
<220> FEATURE:
<223> OTHER INFORMATION: promoter

<400> SEQUENCE: 71
tttatagcta gctcagccct tggtacaatg ctagc                                35

<210> SEQ ID NO 72
<211> LENGTH: 35
<212> TYPE: DNA
<213> ORGANISM: artificial
<220> FEATURE:
<223> OTHER INFORMATION: promoter

<400> SEQUENCE: 72
```
ctgacagcta gctcagtcct aggtataatg ctagc                                35

<210> SEQ ID NO 73
<211> LENGTH: 35
<212> TYPE: DNA
<213> ORGANISM: artificial
<220> FEATURE:
<223> OTHER INFORMATION: promoter

<400> SEQUENCE: 73
tttatggcta gctcagtcct aggtacaatg ctagc                                35

<210> SEQ ID NO 74
<211> LENGTH: 30
<212> TYPE: DNA
<213> ORGANISM: artificial
<220> FEATURE:
<223> OTHER INFORMATION: promoter

<400> SEQUENCE: 74
ttctcaacat aaaaaacttt gtgtaatact                                      30

<210> SEQ ID NO 75
<211> LENGTH: 24
<212> TYPE: DNA
<213> ORGANISM: artificial
<220> FEATURE:
<223> OTHER INFORMATION: primer

<400> SEQUENCE: 75
acgggaacta caagacgcgt gctg                                            24

<210> SEQ ID NO 76
<211> LENGTH: 51
<212> TYPE: DNA
<213> ORGANISM: artificial
<220> FEATURE:
<223> OTHER INFORMATION: primer

<400> SEQUENCE: 76
gctagcactg tacctaggac tgagctagcc gtcaaccggg cctcttgcgg g              51

<210> SEQ ID NO 77
<211> LENGTH: 32
<212> TYPE: DNA
<213> ORGANISM: artificial
<220> FEATURE:
<223> OTHER INFORMATION: primer

<400> SEQUENCE: 77
cagtcctagg tacagtgcta gcccagccag ag                                   32

<210> SEQ ID NO 78
<211> LENGTH: 23
<212> TYPE: DNA
<213> ORGANISM: artificial
<220> FEATURE:
<223> OTHER INFORMATION: primer

<400> SEQUENCE: 78
cctactcagg agagcgttca ccg                                             23

<210> SEQ ID NO 79
<211> LENGTH: 51
<212> TYPE: DNA
<213> ORGANISM: artificial

```
<220> FEATURE:
<223> OTHER INFORMATION: primer

<400> SEQUENCE: 79
gctagcattg tacctaggac tgagctagct ataaaccggg cctcttgcgg g        51

<210> SEQ ID NO 80
<211> LENGTH: 32
<212> TYPE: DNA
<213> ORGANISM: artificial
<220> FEATURE:
<223> OTHER INFORMATION: primer

<400> SEQUENCE: 80
cagtcctagg tacaatgcta gcccagccag ag                              32

<210> SEQ ID NO 81
<211> LENGTH: 28
<212> TYPE: DNA
<213> ORGANISM: artificial
<220> FEATURE:
<223> OTHER INFORMATION: primer

<400> SEQUENCE: 81
gtgactctag tagagagcgt tcaccgac                                   28

<210> SEQ ID NO 82
<211> LENGTH: 56
<212> TYPE: DNA
<213> ORGANISM: artificial
<220> FEATURE:
<223> OTHER INFORMATION: primer

<400> SEQUENCE: 82
ttgacggcta gctcagtcct aggtacagtg ctagctactt gtaacgctag atccgg    56

<210> SEQ ID NO 83
<211> LENGTH: 38
<212> TYPE: DNA
<213> ORGANISM: artificial
<220> FEATURE:
<223> OTHER INFORMATION: primer

<400> SEQUENCE: 83
aggactgagc tagccgtcaa tcgtggccct gcatgcac                        38

<210> SEQ ID NO 84
<211> LENGTH: 29
<212> TYPE: DNA
<213> ORGANISM: artificial
<220> FEATURE:
<223> OTHER INFORMATION: primer

<400> SEQUENCE: 84
gggacaactc cagtgaaaag ttcttctcc                                  29

<210> SEQ ID NO 85
<211> LENGTH: 56
<212> TYPE: DNA
<213> ORGANISM: artificial
<220> FEATURE:
<223> OTHER INFORMATION: primer

<400> SEQUENCE: 85
ctgacagcta gctcagtcct aggtataatg ctagctactt gtaacgctag atccgg    56
```

```
<210> SEQ ID NO 86
<211> LENGTH: 38
<212> TYPE: DNA
<213> ORGANISM: artificial
<220> FEATURE:
<223> OTHER INFORMATION: primer

<400> SEQUENCE: 86
aggactgagc tagccataaa tcgtggccct gcatgcac                                38

<210> SEQ ID NO 87
<211> LENGTH: 56
<212> TYPE: DNA
<213> ORGANISM: artificial
<220> FEATURE:
<223> OTHER INFORMATION: primer

<400> SEQUENCE: 87
tttatggcta gctcagtcct aggtacaatg ctagctactt gtaacgctag atccgg           56

<210> SEQ ID NO 88
<211> LENGTH: 38
<212> TYPE: DNA
<213> ORGANISM: artificial
<220> FEATURE:
<223> OTHER INFORMATION: primer

<400> SEQUENCE: 88
aggactgagc tagccataaa tcgtggccct gcatgcac                                38
```

SYSTEM AND METHODS FOR DETECTING RIBOSOME INHIBITION

CROSS-REFERENCE TO RELATED APPLICATION

This application is the § 371 U.S. National Stage of International Application No. PCT/US2016/035451, filed Jun. 2, 2016, which claims priority to U.S. Provisional Application No. 62/169,637, filed Jun. 2, 2015, each of which is incorporated herein by reference in its entirety.

GOVERNMENT FUNDING

This invention was made with government support under GM103451 awarded by the national Institutes of Health. The government has certain rights in the invention.

SUMMARY

This disclosure describes, in one aspect, a cell genetically modified to detect ribosome inhibition in the cell. Generally, the genetically-modified cell includes an aminoglycoside-sensitive orthogonal 16S rRNA (O-16S) coding region bearing a mutated anti-Shine-Dalgarno (O-ASD) sequence, a repressor/operator system, and a polynucleotide encoding a detectable reporter under transcriptional control of the repressor/operator system. The repressor/operator system includes a coding region that encodes a transcriptional regulator and having an orthogonal SD (O-SD) sequence complementary to the 16S rRNA O-ASD sequence. The operator sequence, which is repressable by the transcriptional regulator, is operably linked to the polynucleotide encoding a detectable reporter.

In some cases, the repressor/operator system can include TetR/PLtetO-1.

In some cases, the detectable signal can include a fluorescent polypeptide such as green fluorescent protein or a variant thereof.

In another aspect, this disclosure describes a method of measuring ribosome inhibition. Generally, the method includes providing any embodiment of the genetically-modified cell summarized above, contacting the cell with a test compound, and detecting a signal produced by the reporter, wherein intensity of the signal indicates a dose dependent degree of ribosome inhibition.

The above summary of the present invention is not intended to describe each disclosed embodiment or every implementation of the present invention. The description that follows more particularly exemplifies illustrative embodiments. In several places throughout the application, guidance is provided through lists of examples, which examples can be used in various combinations. In each instance, the recited list serves only as a representative group and should not be interpreted as an exclusive list.

DETAILED DESCRIPTION OF ILLUSTRATIVE EMBODIMENTS

Figure 1:
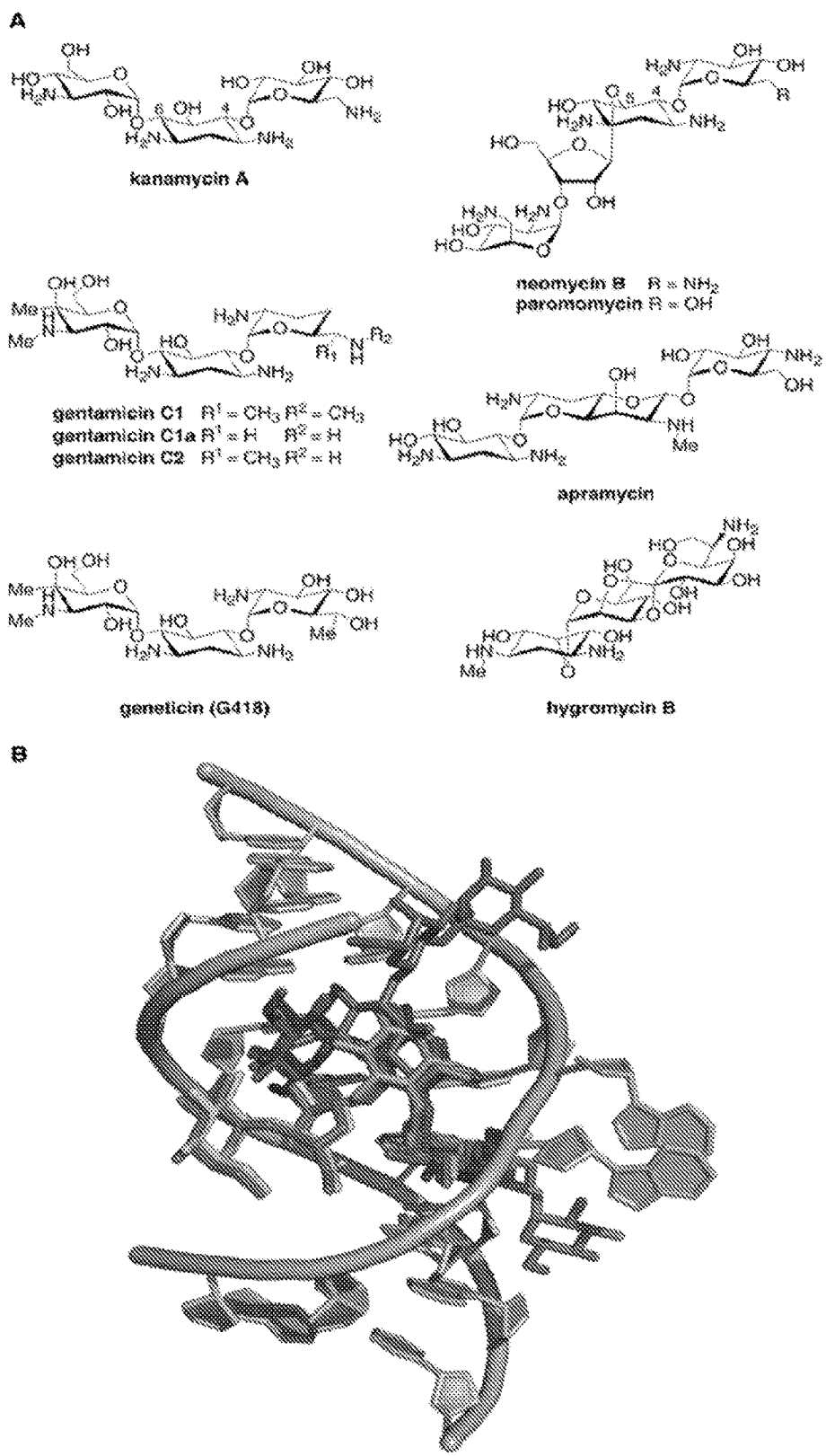
FIG. 1. (A) Structures of aminoglycosides used in this study. (B) Overlayed X-ray crystal structures of the decoding site (A-site) of the E. coli 16S ribosomal RNA (rRNA) with these aminoglycosides bound. Residues 1403-1411, 1489-1498 of 16S rRNA are shown in grey. Aminoglycosides are color-coded as follows; and the source PDB file for each is given in parentheses: kanamycin A: maroon (2ESI[10b]), gentamicin: purple (2QB9[8b]), geneticin (G418): pink (1MWL[10a]), neomycin B: dark green (2QAL[8b]), paromomycin: light green (2Z4K[8b]), apramycin: orange (4AQY[8e]) hygromycin: blue (3DF1[8c]).

The ribosome is a complex, highly conserved biomolecular machine essential for the biosynthesis of cellular proteins and peptides. The essentiality and ancient origin of the ribosome have made it one of the most frequent targets of antibacterial natural products. Aminoglycosides (FIG. 1A) can impair ribosome function by affecting the efficiency of intersubunit rotation, translocation, and/or ribosome recycling. Aminoglycoside also can impair ribosome function by inducing translational miscoding through specific interactions with the decoding site (A-site) of the 16S ribosomal RNA (rRNA) in helix 44 (h44) of the small (30S) ribosomal subunit (FIG. 1B), and in the case of some aminoglycosides, with helix 69 (H69) of the large (50S) ribosomal subunit.

Affinities of aminoglycosides for rRNA hairpins mimicking the decoding site have been assessed using mass spectrometry, surface plasmon resonance (SPR), and competition assays. However, the affinities measured by these methods do not correlate linearly with in vivo antibacterial potencies. The dose-dependent effects of aminoglycosides on translation, on the bulk kinetics of translation, and/or on the kinetics of its individual steps have also been examined in vitro using cell-free translation systems, more recently combined with single molecule techniques such as smFRET. These studies show that although most aminoglycosides exert their effects in large part by binding to the decoding site of h44, individual compounds differ markedly with respect their potencies and in their effects on the kinetics of the individual steps of translation.

In contrast to the breadth of techniques available for in vitro studies, in vivo analyses of the effects of aminoglycosides on translation have been limited to measuring minimum inhibitory concentrations (MICs) of the compounds on wild-type bacterial strains and on those carrying ribosomal resistance mutations. These limitations are the consequence of the essentiality of the ribosome for cell survival. However, the limitations imposed by ribosome essentiality can be circumvented in vivo through the use of orthogonal ribosomes (O-ribosomes)—specialized mutant ribosomes that, by virtue of a mutated 16S rRNA anti-Shine-Dalgarno (ASD) sequence, are unable to translate native mRNA, yet retain the ability to translate mRNA carrying a complementary mutant Shine-Dalgarno (SD) sequence. O-ribosomes, in a properly engineered cellular context, can be used to directly detect and quantify ribosome inhibition by aminoglycosides, providing a means of rapidly assessing the activity, specificity, and/or potency of these compounds in living bacterial cells.

This disclosure describes engineered *E. coli* strains harboring an O-ribosome-controlled fluorescent reporter that are able to detect ribosome inhibition by a variety of aminoglycosides in a highly sensitive, dose-dependent manner with essentially no background. The dose response patterns observed for different aminoglycosides are consistent with current knowledge regarding their potencies and mechanisms of action; and in some cases provide additional insights into the characteristics of specific aminoglycosides. Thus, the O-ribosome reporter system provides a powerful new tool for easily and rapidly assessing the target sites and relative potencies of aminoglycosides and for investigating their mechanisms of action in living bacterial cells.

The exemplary aminoglycoside responsive strains described herein are designed to harbor an engineered plasmid-borne reporter system that includes three elements (FIG. 2A): (1) a constitutively expressed aminoglycoside-sensitive orthogonal 16S rRNA (O-16S) coding region bearing a mutated anti-Shine-Dalgarno (O-ASD) sequence (Lee et al., 1996, *RNA* 2:1270-1285), (2) a repressor/operator system that includes the tetR coding region encoding a constitutively expressed tetracycline-responsive repressor protein TetR (Beck et al., 1982, *J. Bacteriol.* 150:633-642) with orthogonal SD (O-SD) sequence complementary to the 16S rRNA O-ASD sequence (Lee et al., 1996, *RNA* 2:1270-1285) and the TetR-repressed promoter PLtetO-1, and (3) a polynucleotide encoding a detectable reporter—e.g., a gfp-uv polynucleotide encoding the green fluorescent protein variant GFPuv (Crameri et al., 1996, *Nat. Biotech.* 14:315-319)—under transcriptional control of PLtetO-1 (Lutz et al., 1997, *Nucleic Acids Res.* 25:1203-1210). In the absence of aminoglycoside (FIG. 2A, left panel), cells bearing these three elements produce O-ribosome-derived TetR that represses transcription of gfp-uv, resulting in no fluorescence. In the presence of aminoglycoside (FIG. 2A, right panel), however, the O-ribosome is inhibited, resulting in a reduced level of TetR, de-repression of gfp-uv transcription, and production of GFPuv. The system is designed to be highly sensitive by substantially amplifying the aminoglycoside input signal through transcription and translation of gfp-uv, resulting in production of multiple GFPuv proteins per aminoglycoside molecule.

Figure 21:
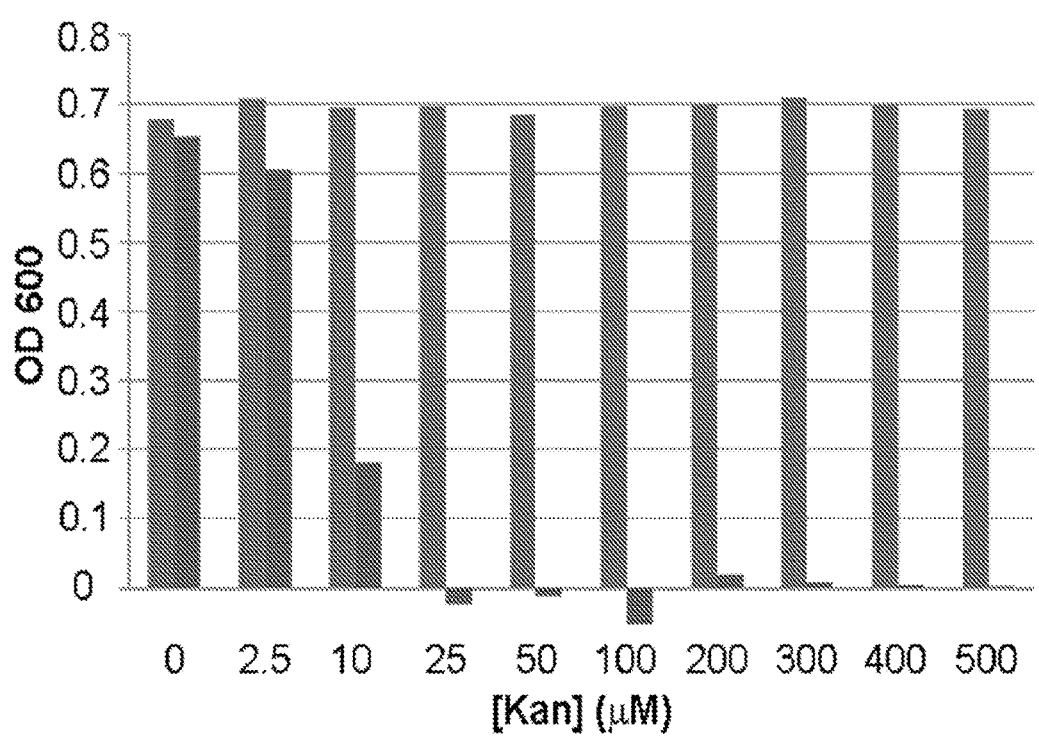
FIG. 21. $OD_{600}$ readings of SH386 (A1408G, blue bars) and SH430 (wild-type, red bars) grown in a range of kanamycin concentrations.

To protect the *E. coli* host itself from inhibition by aminoglycosides, the strain's native rRNA was made aminoglycoside resistant using a previously-developed host, *E. coli* SQ380, in which all seven chromosomal copies of the rRNA operon were deleted and replaced by a single rRNA operon on plasmid prrnC-sacB bearing the counterselectable marker sacB. The A1408G 16S rRNA mutation, which confers resistance to many aminoglycosides, was introduced into rRNA operon-expressing plasmid pRRSH2. The resulting plasmid, pRRSH2-A1408G, was used to replace prrnC-sacB in SQ380. The resulting strain SH386 possessed a high-level of resistance to kanamycin A, up to 500 μM, the highest concentration tested (FIG. 21).

While described herein and illustrated (FIG. 2) in the context of an exemplary embodiment in which the repressor/operator pair includes the TetR/PLtetO-1 system, the constructs and methods described herein can involve any suitable repressor/operator pair. Exemplary alternative repressor/operator pairs include, for example, LacI/Plac, AraC/Para, or any other repressor operator pair that functions analogously to TetR/PLtetO-1.

Similarly, while described herein and illustrated in the context of an exemplary embodiment in which the polynucleotide encoding a detectable reporter encodes a green fluorescent protein variant, the polynucleotide, the constructs and methods described herein can involve any suitable detectable reporter whose expression can be regulated by the repressor/operator pair. Suitable polynucleotides can encode, for example, other fluorescent proteins or peptides, enzymes, or other reported polypeptide.

Figure 2:
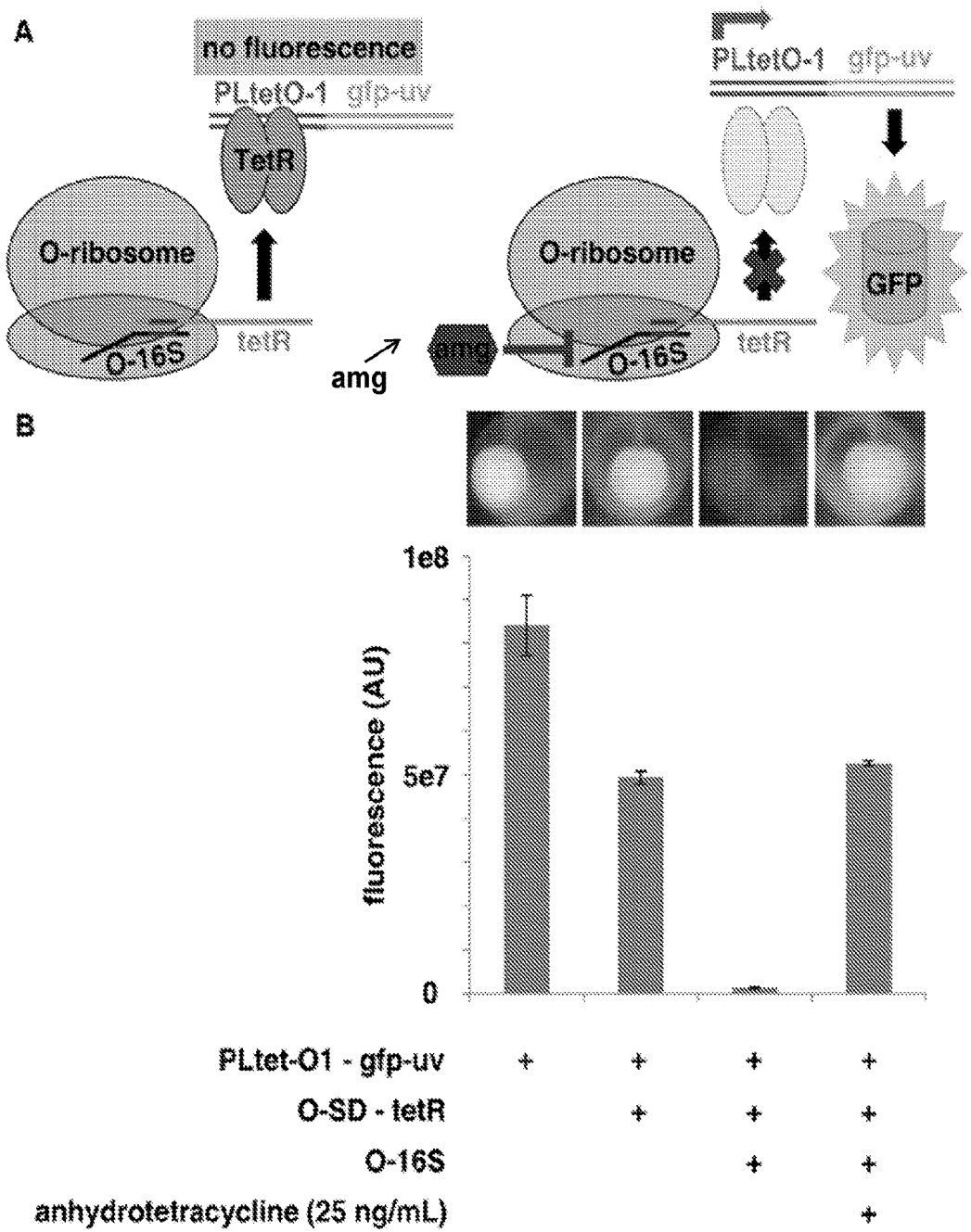
FIG. 2. (A) Schematic showing the functionality of the orthogonal ribosome-controlled fluorescent reporter in the absence (left panel) and presence (right panel) of aminoglycoside. The O-16S rRNA is shown in black, O-SD/O-ASD pair is shown in red, tetR mRNA and TetR protein are shown in cyan, PLtetO-1 is shown in blue, the gfp-uv gene and GFP protein are shown in green, and aminoglycoside is shown as a red hexagon. (B) Cell pellet fluorescence and fluorescence quantification of E. coli DH5α cells transformed with (from left to right) plasmids pGBSH3, pGBSH18, pSH3-KF (see Examples for details).

Similarly, while described herein and illustrated in FIG. 2 in the context of an exemplary embodiment in which an orthogonal ribosome derived from the E. coli 16S ribosomal RNA sequence is employed, the constructs and methods described herein can involve any suitable 16S ribosomal RNA sequence.

Similarly, while described herein and illustrated in FIG. 2 in the context of an exemplary embodiment in which the mutant E. coli strain SQ380 host strain is employed, the constructs and methods described herein can involve any suitable host strain.

To protect the E. coli host itself from inhibition by aminoglycosides, the strain's native rRNA was made aminoglycoside resistant using a previously-developed host, E. coli SQ380, in which all seven chromosomal copies of the rRNA operon were deleted and replaced by a single rRNA operon on plasmid prrnC-sacB bearing the counterselectable marker sacB. The A1408G 16S rRNA mutation, which confers resistance to many aminoglycosides (Recht et al., 1999, EMBO J. 18:3133-3136), was introduced into rRNA operon-expressing plasmid pRRSH2. The resulting plasmid, pRRSH2-A1408G, was used to replace prrnC-sacB in SQ380. The resulting strain SH386 possessed a high-level of resistance to kanamycin (up to 500 μM, the highest concentration tested).

Figure 10:
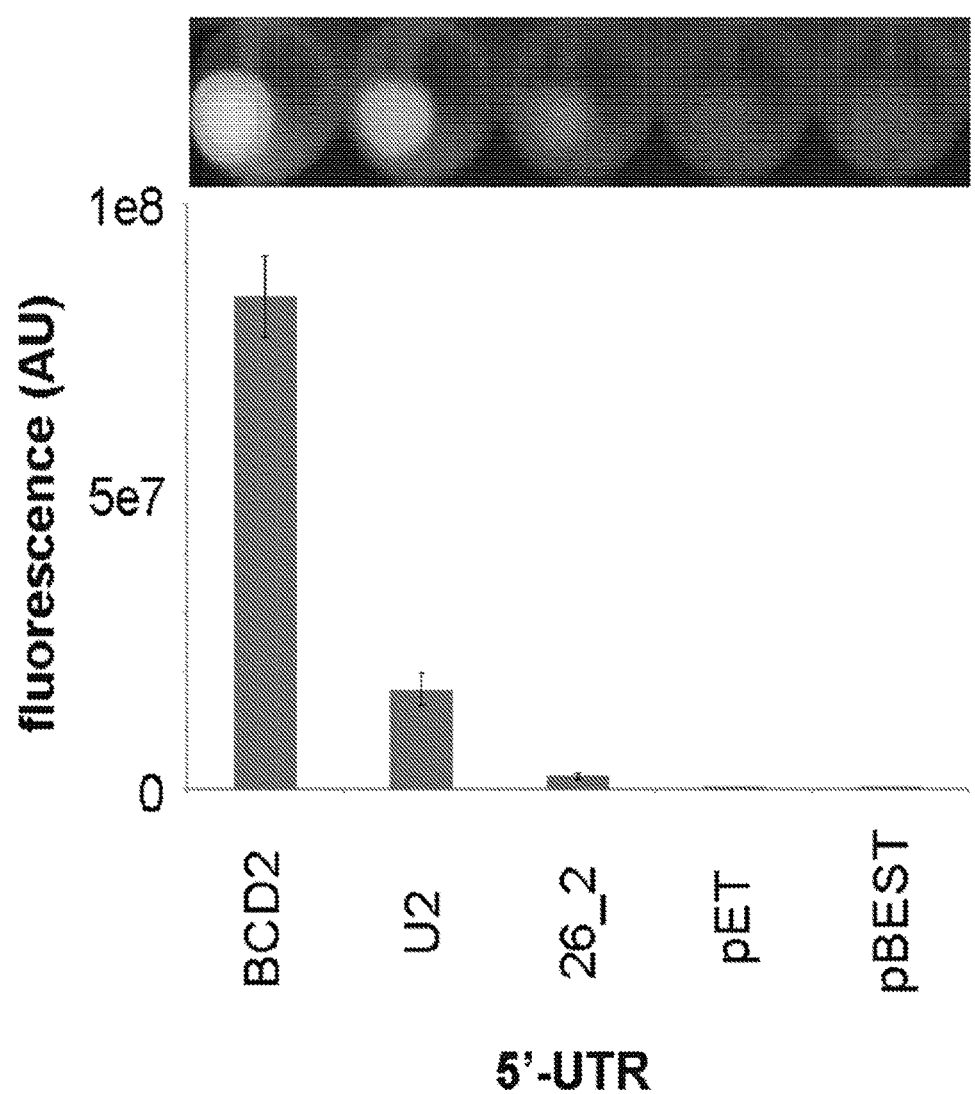
FIG. 10. Cell pellet fluorescence and fluorescence quantification of pGBSH1 variants in which the gfp-uv 5'-UTR has been altered.
Figure 16:
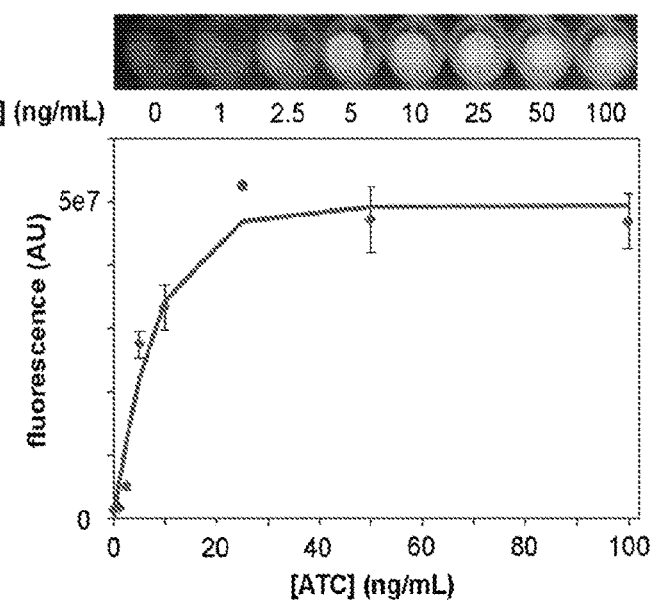
FIG. 16. Cell pellet fluorescence and fluorescence quantification of E. coli DH5α cells containing pSH3-KF grown in the presence of a range of anhydrotetracycline concentrations.

To demonstrate that the reporter system functions properly, plasmids harboring sets of the system's three functional elements were sequentially constructed and assayed individually by expression in E. coli DH5α and fluorescence quantification (FIG. 2B). First, performance of the element bearing gfp-uv under control of PLtetO-1 with the optimized 5'-untranslated region BCD2 (Mutilak et al., 2013, Nat. Methods 10:354-360) (see FIG. 10 and Examples section 2.3.4 for optimization) was examined. In the absence of tetR, PLtetO-1 behaves as a strong constitutive promoter and results in high GFP expression (FIG. 2B). Next, the O-SD-controlled tetR cassette was inserted into the gfp-uv-expressing construct. The resulting two element system retained robust fluorescence (~60% of that of the gfp-uv-expressing construct, FIG. 2B). Finally, the O-16S cassette was inserted into the gfp-uv/tetR-expressing construct to give final reporter construct pSH3-KF. Addition of the O-16S cassette completely abolished fluorescence (FIG. 2B). Fluorescence could be completely recovered, however, by adding a saturating concentration of anhydrotetracycline (ATC), which binds to TetR causing its dissociation from PLtetO-1 (FIG. 2B, FIG. 16). Together, these results indicate that the reporter system as a whole, as well as its individual elements, function correctly in E. coli DH5α. The ~40% loss of fluorescence upon insertion of the tetR cassette may be due, at least in part, to a polar effect on gfp-uv expression by tetR—not a lack of O-SD orthogonality—since addition of saturating ATC to the pSH3-KF-expressing strain resulted in a fluorescence level nearly identical to (106.6%±1.2%) that observed in the gfp-uv/tetR-expressing strain. Thus, tetR is not translated to a significant extent without co-expression of the O-16S gene.

Figure 3:
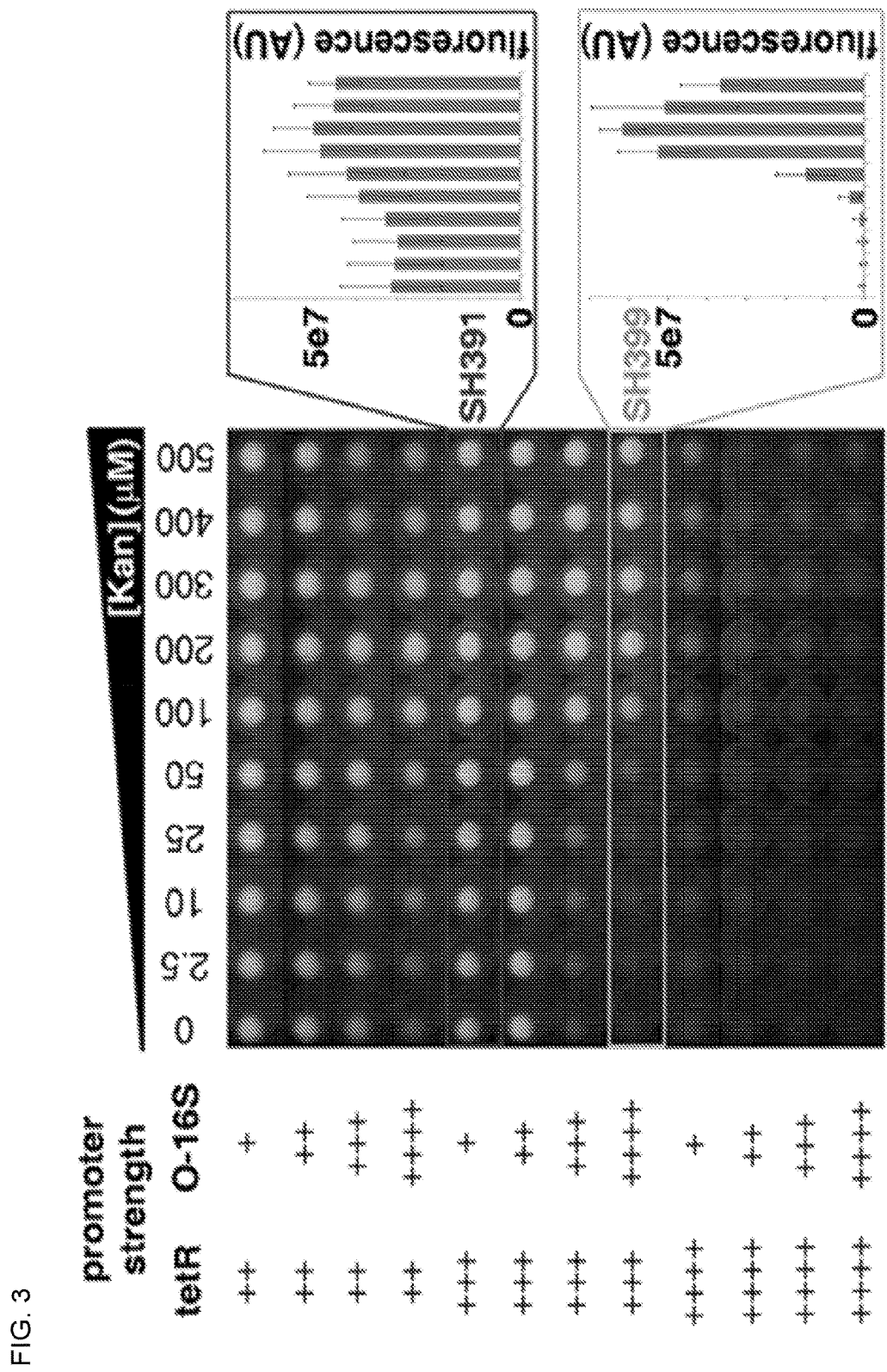
FIG. 3. Cell pellet fluorescence of initial detector strain E. coli SH391 (boxed in red), eleven additional strains with tetR and O-16S promoter strengths combinatorially altered (promoter strengths are show on the left: +– very weak, ++– weak, +++– medium, ++++– strong), and E. coli SH399, the strain with the best detection performance (boxed in green), in response to increasing concentrations of kanamycin. Fluorescence quantification of E. coli SH391 and E. coli SH399 at each of the ten kanamycin concentrations tested is shown in the bar graphs to the right.
Figure 19:
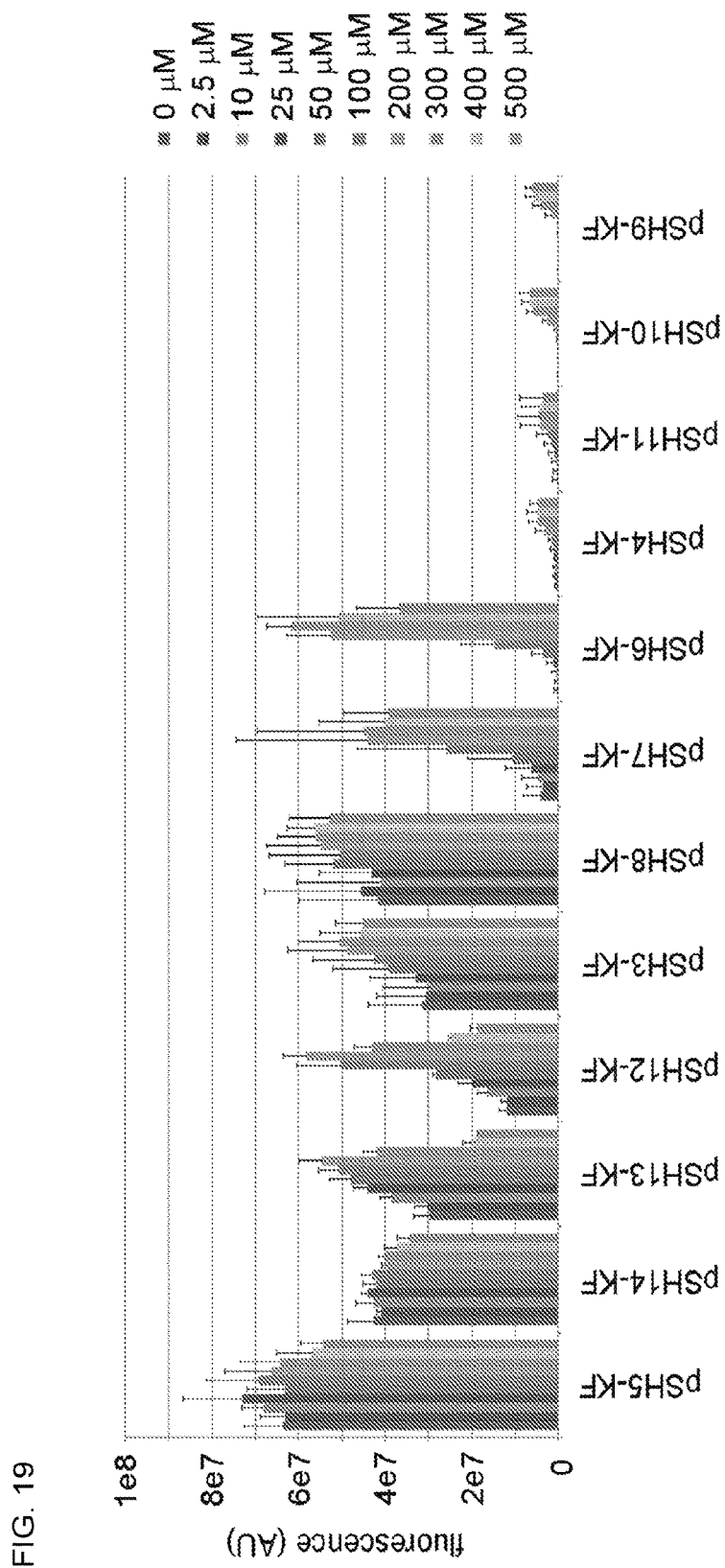
FIG. 19. Fluorescence quantification of E. coli SH386 cells containing pSH3-KF-pSH14-KF grown in the presence of a range of kanamycin concentrations.

In an initial O-ribosome inhibition assay using kanamycin, E. coli SH391 (SH386 transformed with pSH3-KF) showed a modest concentration-dependent increase in fluorescence upon addition of kanamycin (maximum 1.6-fold induction, FIG. 3), but displayed strong background fluorescence in the absence of kanamycin. The promoter strengths of the tetR and O-16S elements, both of which can affect the amount of TetR, were combinatorially altered using synthetic constitutive promoters with characterized strengths (see Examples section 2.4.2). Eleven new pSH3-KF derivatives with altered tetR and O-16S promoter strengths were generated and their performance examined in SH386 (FIG. 3, FIG. 19). One variant strain, SH399, with reporter plasmid pSH6-KF carrying strong promoter BBa_J23100 controlling O-16S expression, had essentially no background and displayed a robust dose-dependent increase in fluorescence (FIG. 3). Cells expressing the twelve pSH3-KF variants showed a range of kanamycin-dependent phenotypes that correlate with promoter strength—from high background and low sensitivity with weak promoter combinations to low background and high sensitivity with strong promoter combinations (FIG. 3). Thus, a combinatorial approach was used to identify the promoter pair that gave optimal detection of ribosome inhibition by kanamycin while eliminating background signal.

Figure 20:
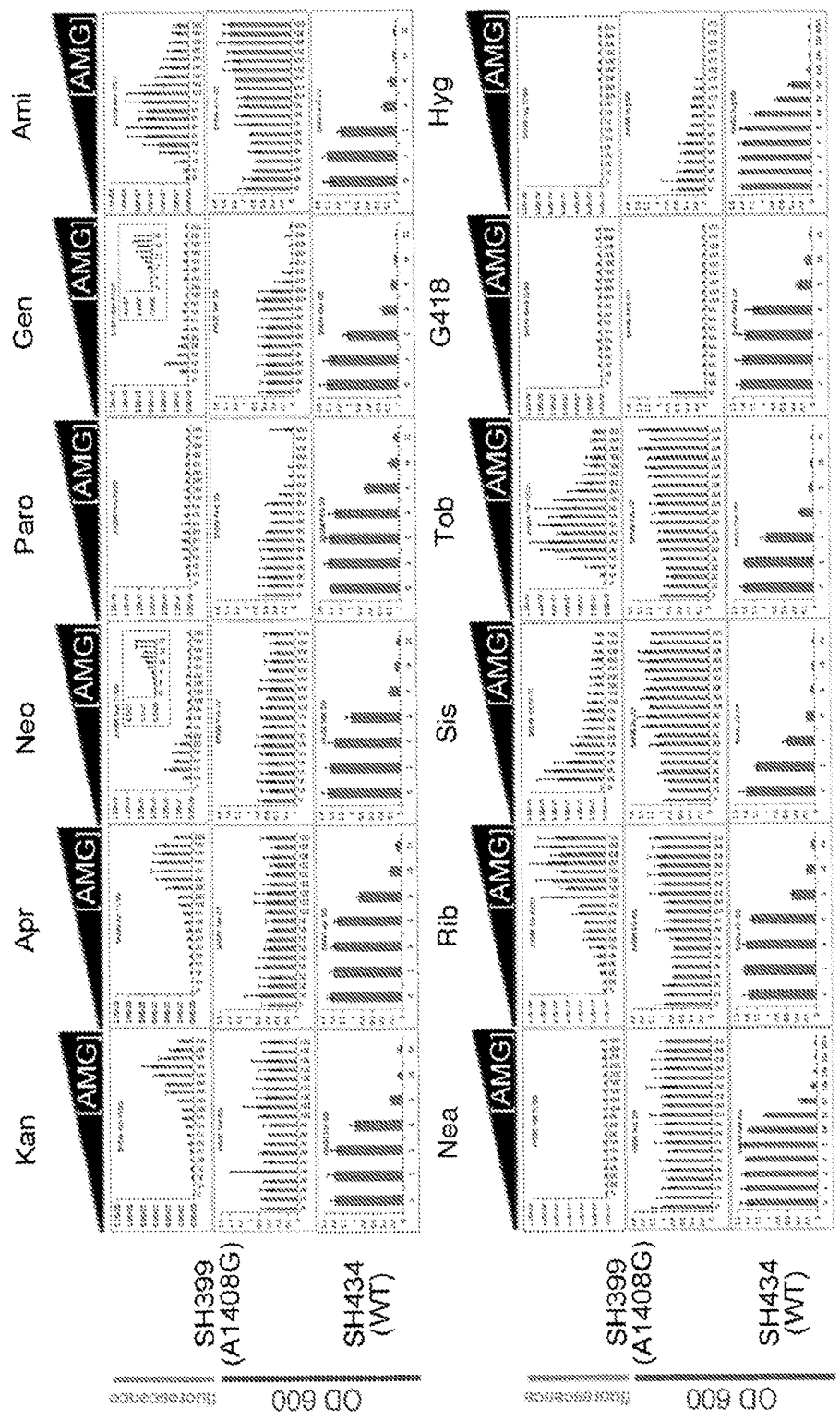
FIG. 20. $OD_{600}$ and fluorescence quantification of E. coli SH399 (pSH6-KF, pRRSH2-A1408G), SH431 (pSH6-KF, pRRSH2-U1406A), and SH434 (pSH6-KF, pRRSH2) cells grown in a range of concentrations (0-500 μM) of each of the seven aminoglycosides examined. The scale of x and y axes is consistent on each bar chart. Undetermined data points are marked with red boxes.

The ability of SH399 to detect ribosome inhibition by other aminoglycosides was tested next. A panel of six additional structurally diverse aminoglycosides, including other 4,6-disubstituted 2-deoxystreptamines (2-DOS) gentamicins and G418, 4,5-disubstituted 2-DOS paromomycin and neomycin, and atypical 2-DOS apramycin and hygromycin (FIG. 1A) were chosen. In addition to kanamycin, SH399 was able to detect O-ribosome inhibition by four of these compounds: apramycin, neomycin, paromomycin, and gentamicins (FIG. 4A). The two compounds that failed to give signal, G418 and hygromycin, also caused significant growth inhibition of SH399 (FIG. 20), indicating that the A1408G 16S rRNA mutation does not confer sufficient resistance to these compounds to allow survival of the detector strain. For those compounds that were detectable, the A1408G mutation confers resistance well above the detection threshold (FIG. 20). Moreover, dose-dependent fluorescence response patterns were different for each compound, with gentamicin, neomycin, and paromomycin giving robust fluorescence responses at low concentrations, and kanamycin and apramycin showing more gradual dose-dependent fluorescence increases. These dose-response patterns correlate well with previously determined potencies ($IC_{50}$ values) of these compounds measured through inhibition of translation in vitro (Sucheck et al., 2000, J. Am.

*Chem. Soc.* 122:5230-5231), demonstrating that the O-ribosome reporter system can be used to assess relative potencies of various aminoglycosides.

Figure 22:
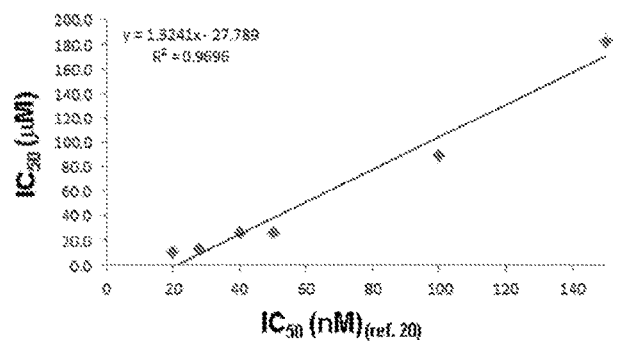
FIG. 22. Analysis of the correlations between: (top table and graph) $IC_{50}$ values previously determined through in vitro translation assays (main text, ref. 28) (column 1, x axis) and $IC_{50}$ values determined from *E. coli* SH399-derived fluorescence data (column 2, y axis); (middle table and graph) $LD_{50}$ values determined from growth inhibition assays of *E. coli* SH434 (column 1, x axis) and $IC_{50}$ values determined from *E. coli* SH399-derived fluorescence data for the subset of six compounds for which there was a statistically significant correlation (column 2, y axis); and (bottom table and graph) $LD_{50}$ values determined from growth inhibition assays of *E. coli* SH434 (column 1, x axis) and $IC_{50}$ values determined from *E. coli* SH399-derived fluorescence data for the full set of 9 compounds (column 2, y axis). The three compounds that produced outlying data are labeled in the graph. Neamine was excluded from the analysis due to its very weak ribosome inhibition and growth inhibition activities.
Figure 22:
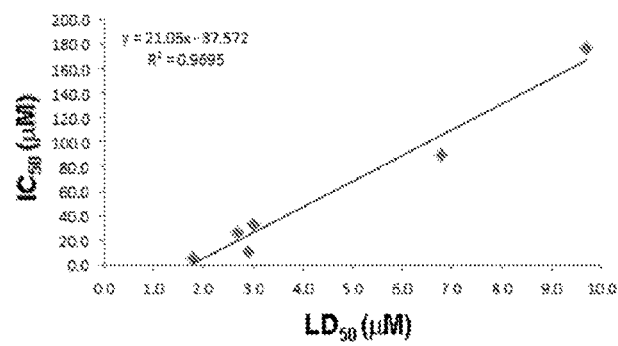
Figure 22:
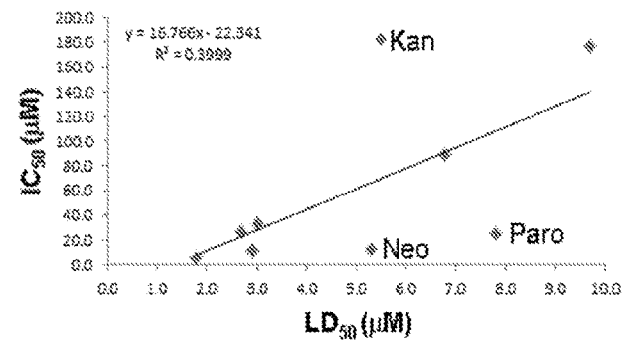

There was a strong correlation ($R^2$=0.97, FIG. 22) between the two datasets, suggesting that $IC_{50}$ values determined using the O-ribosome reporter assay are comparably accurate to those determined using in vitro translation assays. Next, to test whether the fluorescence dose-response patterns also correlate with inhibition of *E. coli* growth, dose-dependent growth inhibition (represented as $LD_{50}$ values) of the parent aminoglycoside-sensitive *E. coli* strain SH434 was compared to $IC_{50}$ values calculated from fluorescence data obtained from aminoglycoside-treated SH399. While data obtained by the two methods correlated for a subset of the compounds (apramycin, gentamicins, amikacin, ribostamycin, sisomicin, and tobramycin; $R^2$=0.97, FIG. 22), there was a lack of correlation between the two datasets for kanamycin A, neomycin B, and paromomycin, and therefore between the two datasets as a whole ($R^2$=0.40, FIG. 22). While the reason for the incomplete correlation between inhibition of *E. coli* growth and fluorescence-derived $IC_{50}$ values is unclear, these inconsistencies may be the result of differences between the pleiotropic effects of differentially inhibiting the ribosome—whose activity is required for synthesis of the entire *E. coli* proteome—on cell viability and/or the effects of differentially inhibiting the O-ribosome, which are restricted to the TetR-GFP output system. Taken together, these results are consistent with the ability of the O-ribosome reporter system to compare the potencies of aminoglycosides as ribosome inhibitors. Of the ten compounds examined, sisomicin was found to have the strongest ribosome inhibition activity, followed in order of decreasing activity by gentamicins, neomycin B, paromomycin, tobramycin, amikacin, ribostamycin, apramycin, kanamycin A, and neamine (FIG. 20 and FIG. 22). These results provide a complete comparative assessment of the ribosome inhibiting potencies of these ten compounds.

Also, at drug concentrations beyond those that give the peak response, fluorescence decreases significantly with neomycin, paromomycin, and gentamicin, but not with kanamycin or apramycin. These decreases in fluorescence were accompanied by growth inhibition in the cases of paromomycin and gentamicin. This result is consistent with the previous observation that neomycin, paromomycin, and gentamicins bind to and inhibit the ribosome at a second, lower affinity site in helix 69 of the large ribosomal subunit. In the O-ribosome reporter described herein, binding to this site on the pRRSH2-A1408G-derived ribosome can affect translation of both GFPuv and endogenous proteins, leading to both a decrease in fluorescence and loss of cell viability. Thus, the O-ribosome reporter system is able to distinguish aminoglycosides that bind exclusively to the h44 site from those that bind to both h44 and H69 sites.

Figure 23:
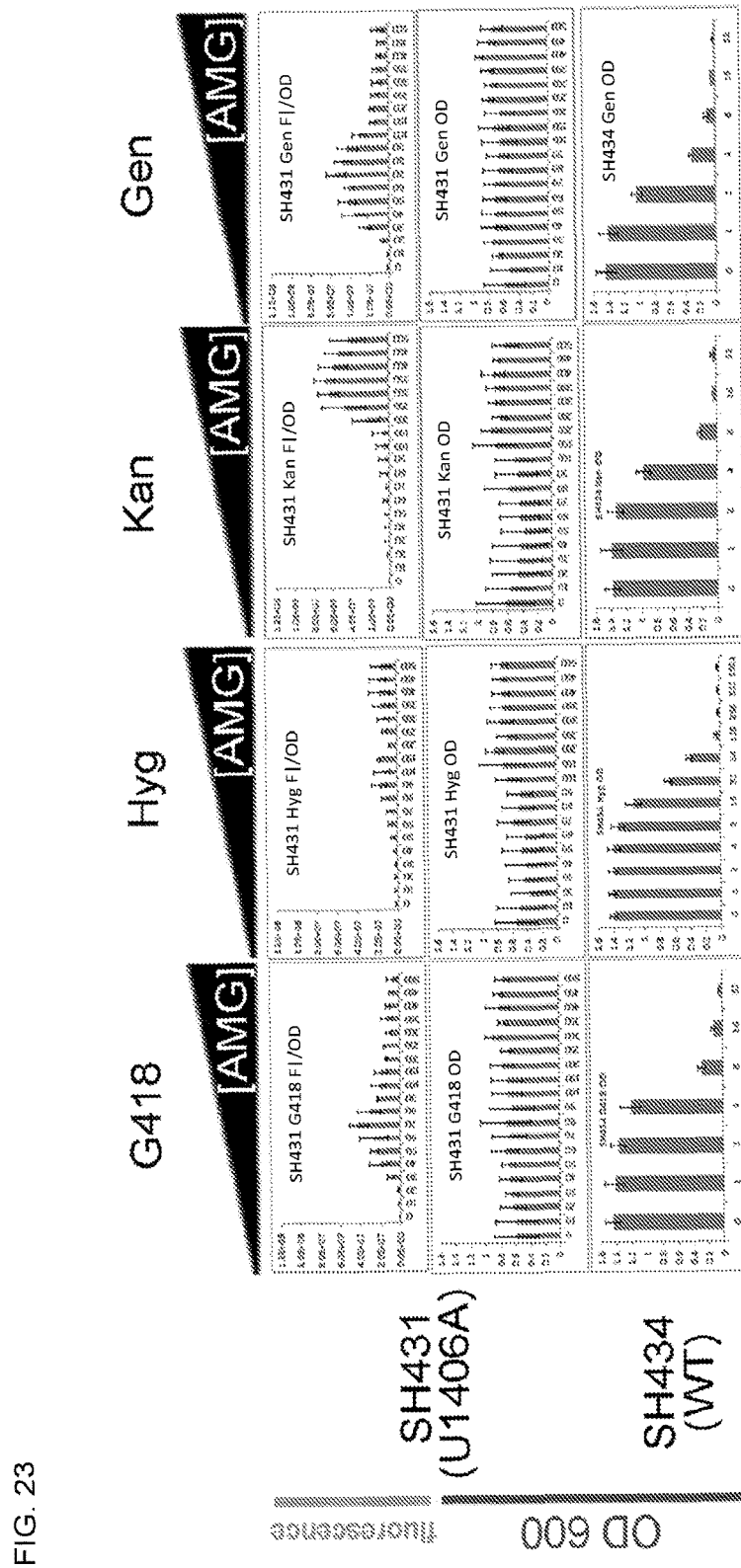
FIG. 23. Fluorescence quantification (top row of graphs) and $OD_{600}$ quantification (bottom row of graphs) of *E. coli* SH431 (pSH6-KF, pRRSH2-U1406A) cells grown in a range of concentrations (0-500 μM) of G418, hygromycin, kanamycin, and gentamicins. The scale of x and y axes is consistent for each row of bar charts.
Figure 24:
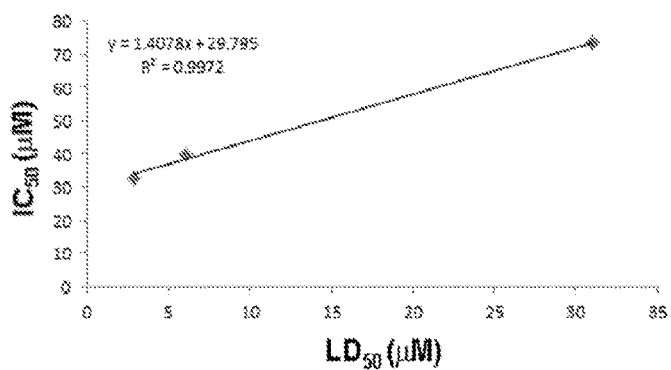
FIG. 24. Analysis of the correlations between: (top table and graph) $LD_{50}$ values determined from growth inhibition assays of *E. coli* SH434 (column 1, x axis) and $IC_{50}$ values determined from *E. coli* SH431-derived fluorescence data for the subset of three compounds for which there was a statistically significant correlation (column 2, y axis); and (bottom table and graph) $LD_{50}$ values determined from growth inhibition assays of *E. coli* SH434 (column 1, x axis) and $IC_{50}$ values determined from *E. coli* SH431-derived fluorescence data for the full set of four compounds (column 2, y axis). The compound that produced outlying data is labeled in the graph.
Figure 24:
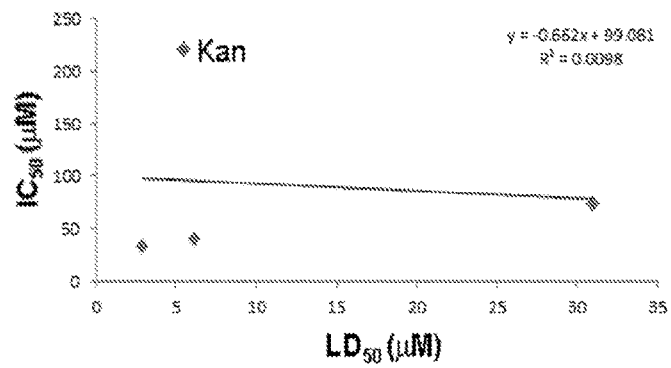

To further explore the capabilities of the system and attempt to develop a strain that can detect O-ribosome inhibition by hygromycin and G418, the U1406A mutation was introduced into pRRSH2. Mutations at position 1406 confer an aminoglycoside resistance spectrum distinct from that of A1408G, including resistance to G418 (U1406A) and hygromycin (U1406C). Strain SH431, carrying this mutation and reporter plasmid pSH6-KF, was tested for its ability to detect O-ribosome inhibition by the same twelve aminoglycosides. SH431 was able to detect O-ribosome inhibition by both G418 and hygromycin as well as by gentamicins and kanamycin (FIG. 4B and FIG. 23). As in the case of treatment of SH399 with some aminoglycosides, a lack of signal by SH431 in the presence of apramycin, neomycin, and paromomycin was observed, and is the result of the inability of the U1406A mutation to confer resistance to these compounds (FIG. 20). Dose-dependent decreases in response at higher concentrations of gentamicins and G418 (FIG. 4B and FIG. 20) were also observed, consistent with binding of gentamicins to the second, low affinity site in H69. The decrease in response with G418 suggests that it, being a close congener of gentamicin, also inhibits the ribosome by binding to the H69 site. Dose response patterns observed for SH431 treated with the four compounds for which fluorescence could be observed indicate that, among these, gentamicins are the most potent ribosome inhibitors, followed by G418 and hygromycin B, with kanamycin A being the least potent (FIG. 23 and FIG. 24). $IC_{50}$ values calculated from the O-ribosome-based fluorescence assay correlated with $LD_{50}$ values of the parent aminoglycoside sensitive *E. coli* strain SH434 for three of the compounds (gentamicins, G418, hygromycin B; $R^2$=0.997, FIG. 24), but not for kanamycin A, as was the case with SH399.

Figure 4:
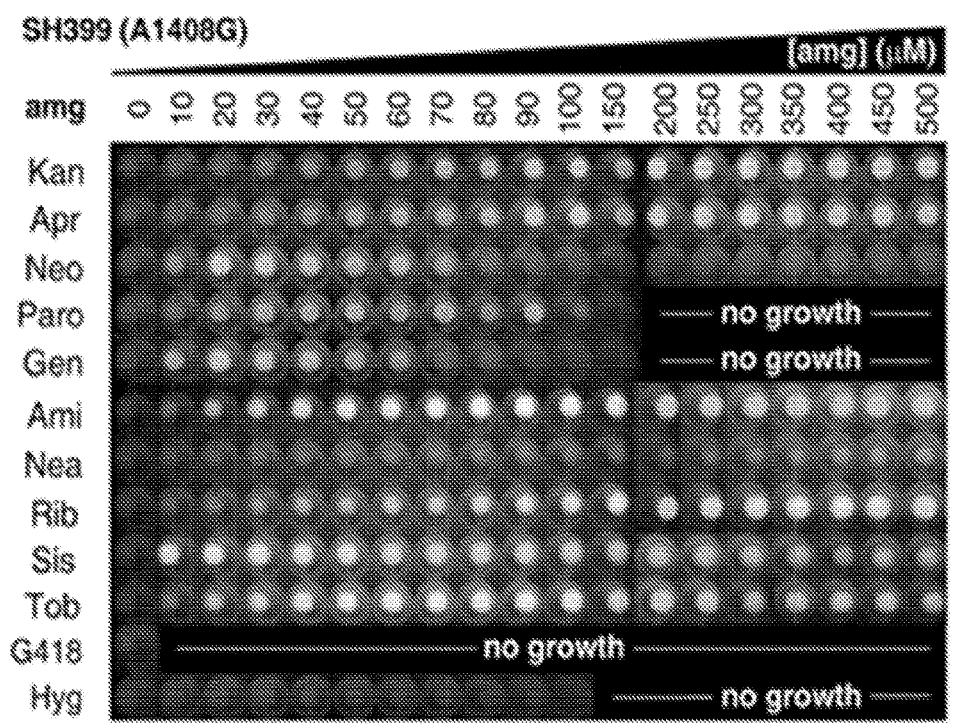
FIG. 4. Cell pellet fluorescence of (A) E. coli SH399 and (B) E. coli SH431 in response to increasing concentrations of each of seven aminoglycosides. Kan: kanamycin A, Apr: apramycin, Neo: neomycin B, Paro: paromomycin, Gen: gentamicin, Ami: amikacin, Nea: neamine, Rib: ribostamycin, Sis: sisomicin, Tob: tobramycin G418: geneticin (G418), Hyg: hygromycin.
Figure 4:
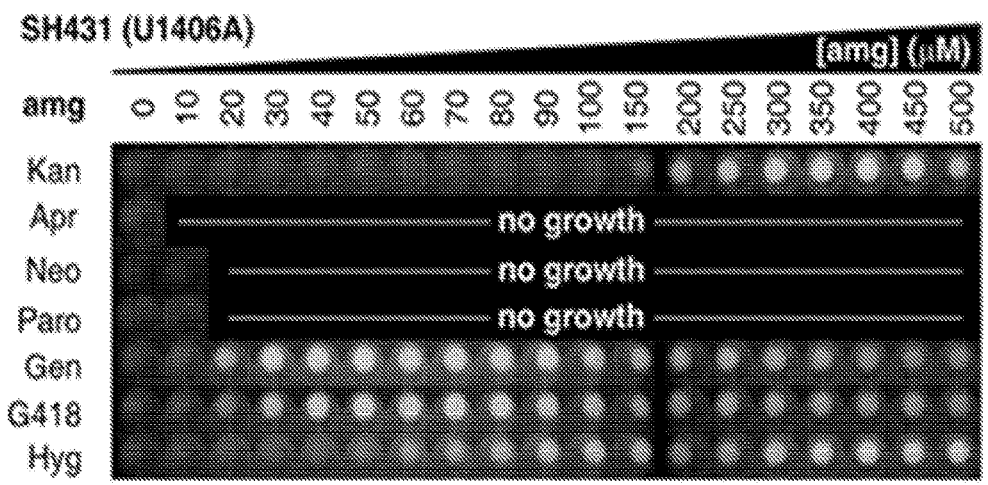

While described herein and illustrated in FIG. 4 in the context of exemplary embodiments in which the ribosomal RNA mutations conferring drug resistance, A1408G and U1406A, were employed, the constructs and methods described herein can involve any suitable ribosomal RNA mutation that confers resistance to a ribosome inhibiting drug.

In summary, this disclosure describes an engineered *E. coli* strain that can directly detect ribosome inhibition by a variety of structurally distinct aminoglycosides with high sensitivity and essentially no background. The dose-response patterns observed for the aminoglycosides tested correlate well with their reported potencies and mechanisms of action, demonstrating that the system can be used to determine relative potencies of aminoglycosides and to make inferences about their mechanisms of action based on similarity of response patterns to those of well-studied aminoglycosides. The selectivity of each strain for detecting specific aminoglycosides—even those with high structural similarity such and gentamicins and G418—can be controlled by employing 16S rRNA mutations that confer distinct resistance profiles.

The O-ribosome reporter strategy described herein can be used to assess in vivo potencies of synthetic aminoglycoside analogs in high-throughput, to detect and quantify aminoglycosides in natural product extracts, and/or to detect activity of aminoglycoside biosynthetic enzymes. The O-ribosome reporter system can be extended to detect ribosome inhibition by other classes of 16S rRNA-targeting inhibitors such as, for example, tetracyclines, tuberactinomycins, and/or pactamycins by employing 16S rRNA resistance mutations specific to each compound class. Mutation of the O-ribosome A-site in the strains described here to mimic the A-site of other bacteria (e.g. Mycobacteria or other pathogens) or human mitochondria may allow estimation of aminoglycoside potency against these bacteria, or toxicity to human cells, respectively.

In the preceding description and following claims, the term "and/or" means one or all of the listed elements or a combination of any two or more of the listed elements; the terms "comprises," "comprising," and variations thereof are to be construed as open ended—i.e., additional elements or steps are optional and may or may not be present; unless otherwise specified, "a," "an," "the," and "at least one" are used interchangeably and mean one or more than one; and the recitations of numerical ranges by endpoints include all numbers subsumed within that range (e.g., 1 to 5 includes 1, 1.5, 2, 2.75, 3, 3.80, 4, 5, etc.).

In the preceding description, particular embodiments may be described in isolation for clarity. Unless otherwise expressly specified that the features of a particular embodiment are incompatible with the features of another embodiment, certain embodiments can include a combination of compatible features described herein in connection with one or more embodiments.

For any method disclosed herein that includes discrete steps, the steps may be conducted in any feasible order. And, as appropriate, any combination of two or more steps may be conducted simultaneously.

The present invention is illustrated by the following examples. It is to be understood that the particular examples, materials, amounts, and procedures are to be interpreted broadly in accordance with the scope and spirit of the invention as set forth herein.

EXAMPLES

1. Materials and Methods

1.1. General.

All general molecular biological and biochemical reagents, including Luria-Bertani (LB) media (Miller), were purchased from VWR (Atlanta, Ga.) and were used without further purification. Water used for media was obtained from a Barnstead/Thermolyne HN Ultrapure water purification system. Gentamicins sulfate, paromomycin sulfate, geneticin (G418) sulfate, neomycin sulfate, and hygromycin B were purchased from Santa Cruz Biotechnology (Dallas, Tex.). Kanamycin sulfate was purchased from Genlantis (San Diego, Calif.). Apramycin sulfate was purchased from Research Products International (Mount Prospect, Ill.). Restriction enzymes, Phusion DNA polymerase, T4 DNA ligase and calf intestinal alkaline phosphatase were purchased from New England Biolabs (Ipswich, Mass.). DNA purification and concentration was performed using the DNA Clean & Concentrator Kit; and agarose gel DNA extraction was performed using the Gel DNA Recovery Kit, both from Zymo Research (Irvine, Calif.). Plasmid extractions were performed using the QIAprep Spin Miniprep Kit from Qiagen (Valencia, Calif.). Oligonucleotides were obtained from Integrated DNA Technologies (Coralville, Iowa). DNA sequencing was performed by Genewiz (South Plainfield, N.J.). PCR reactions were carried out using a Bio-Rad S1000 thermal cycler. Cell density and fluorescence measurements were taken using a Molecular Devices SpectraMax M2 Multi-Mode Microplate Reader. Plasmid and DNA sequence design and management was conducted using Vector NTI 10 (Life Technologies). Chemically competent E. coli cells were prepared using the rubidium chloride method.[1] Standard molecular biological methods, protocols, reagents, and materials[1] were used for PCR, restriction enzyme digestion, ligation, transformation, selection of transformants, agarose gel electrophoresis, gel extraction, and plasmid isolation unless otherwise specified.

1.2. Bacterial Strains.

E. coli DH5α and E. coli TOP10 were used for routine DNA cloning and manipulation. E. coli SQ380 (E. coli MG1655/ΔrrnGADEHBC/prrnC-sacB²/ptRNA67²), in which all seven genomic rRNA operons have been deleted and replaced with a single plasmid-borne rRNA operon expressed from the sucrose counterselectable plasmid prrnC-sacB, was used as the starting point for construction of strains capable of detecting ribosome inhibition by aminoglycoside antibiotics.

1.3. Bacterial Culture.

Routine liquid culture of E. coli DH5α and E. coli TOP10 for cloning purposes was carried out in 2-5 mL of Luria-Bertani broth in sterile 15 mL conical tubes at 37° C., 250 rpm overnight (12-16 h). Selection of E. coli DH5α and E. coli TOP10 transformants was carried out on Luria-Bertani agar plates containing the appropriate antibiotic(s) at 37° C. overnight (12-16 h). All cell growth and fluorescence assays were performed in sterile Cellstar 96-well deep well culture plates sealed with breathable sealing film, with one mL of LB media per well and with appropriate concentrations of the necessary antibiotics (100 μg/mL ampicillin, 35 μg/mL chloramphenicol, 50 μg/mL kanamycin, 100 μg/mL spectinomycin), anhydrotetracycline (1-100 ng/mL) and aminoglycoside (2.5-500 μM).

1.4. General PCR Conditions.

Concentrations of template, primers, polymerase, dNTPs, and buffer recommended by NEB for Phusion DNA polymerase were used unless otherwise specified. Four types of PCR protocols were used to construct all fragments and all final constructs not obtained by ligation: Protocol 1: PCR amplification of a single fragment with two primers, Protocol 2: templateless (primer only) assembly with three primers, Protocol 3: two fragment overlap extension PCR, and Protocol 4: COE-PCR (see Section 2.2.1 for an explanation of this method). General PCR programs for each protocol are given below.

Protocol 1

| | |
|---|---|
| 98° C. | 30 seconds |
| 98° C. | 10 seconds |
| Tm-prim*-5° C. | 30 seconds |
| 72° C. | 30 sec/kb |
| Repeat two times | |
| 98° C. | 10 seconds |
| Tm-ext#-5° C. | 30 seconds |
| 72° C. | 30 sec/kb |
| Repeat 26 times | |
| 72° C. | 10 minutes |
| 4° C. | storage |

Protocol 2

Same as Protocol 1, but with no template and with 0.1 μM inside primer and 0.5 μM of each outside primer.

Protocol 3

| | |
|---|---|
| 98° C. | 30 seconds |
| 98° C. | 10 seconds |
| Tm-OE^-5° C. | 30 seconds |
| 72° C. | 30 sec/kb |
| Repeat 1-9 times (primerless) | |
| Add 0.5 μM of two outside primers | |
| 98° C. | 10 seconds |
| Tm-ext#-5° C. | 30 seconds |
| 72° C. | 30 sec/kb |
| Repeat 29 times | |
| 72° C. | 10 minutes |
| 4° C. | storage |

Protocol 4

Using 10 nM of each fragment. Fragment junctions designed to have Tm of 55° C.+/−5° C.

| | |
|---|---|
| 98° C. | 30 seconds |
| 98° C. | 10 seconds |

| | |
|---|---|
| 48° C.-50° C. | 30 seconds |
| 72° C. | 15 sec/kb (of final plasmid size) |
| Repeat 29-34 times | |
| 72° C. | 10 minutes |
| 4° C. | storage |

*Tm-prim = Tm of the portion of the primer that primes to the template
Tm-ext = Tm of the entire primer
^Tm-OE = Tm of the junction between fragments 1.5. Enforced Replacement by Sucrose Counterselection To replace plasmid prrnC-sacB ($Kan^R$, $Suc^S$), which is essential in *E. coli* SQ380 because it carries the only cellular copy of the ribosomal RNA (rRNA) operon, with pRRSH2 ($Amp^R$), pRRSH2-A1408G, or pRRSH2-U1406A, sucrose counterselection was used against the sacB (sucrose sensitivity gene)-containing plasmid prrnC-sacB. *E. coli* SQ380 competent cells were grown in LB with kanamycin and spectinomycin (essential tRNA-bearing plasmid ptRNA67 has a spectinomycin resistance marker) and transformed with pRRSH2, pRRSH2-A1408G, or pRRSH2-U1406A. Transformants were selected on LB agar with ampicillin and spectinomycin. One colony was picked and grown in LB liquid with ampicillin and spectinomycin overnight, and plated on LB agar with ampicillin, spectinomycin, and 5% (w/v) sucrose. Surviving colonies are resistant to both ampicillin and sucrose, and have therefore gained pRRSH2 and lost prrnC-sacB. Elimination of prrnC-sacB was verified by plasmid isolation and digestion of the resulting plasmid mixture with PvuI, which has three recognition sites in prrnC-sacB but only a single site in pRRSH2 and ptRNA67, and therefore gives a distinctive digestion pattern if prrnC-sacB is present. This, rather than replica plate screening of surviving colonies for kanamycin sensitivity, was done because pRRSH2-A1408G and pRRSH2-U1406A confer kanamycin resistance. The resulting strains—SH430 containing pRRSH2, SH386 containing pRRSH2-A1408G, and SH424 containing pRRSH2-U1406A—were used for transformation with plasmids carrying the O-ribosome-based aminoglycoside detection systems (pSH3-KF through pSH14-KF).

1.6. Cell Density and Fluorescence Assays.

All cell density and fluorescence measurements were taken in triplicate. 96-well culture plates (1 mL LB per well) with appropriate concentrations of necessary antibiotics and aminoglycoside were inoculated 1:100 from a saturated overnight liquid culture and allowed to grow for 48 hours at 37° C., 200 rpm shaking. For cell density assays, 40 µL of sample was taken from each well, diluted 5-fold, and $OD_{600}$ was measured by microplate reader. The $OD_{600}$ of the original culture was calculated by multiplying the reading by the dilution factor (Melançon et al., 2009, *Bioorg. Med. Chem. Lett.* 19:3845-3847). For cell pellet fluorescence imaging, cells were pelleted by centrifugation (4,000×g, 15 minutes, 4° C.) and the supernatant was decanted completely. The underside of the plate was illuminated at 365 nm using an ultraviolet handheld lamp and photgraphed with an 8 megapixel digital camera. For fluorescence quantification, cell pellets were resuspended in 1 mL of ¼×Ringer's solution (30.75 mM NaCl, 1.2 mM, KCl, 1.5 mM $CaCl_2$, pH 7.3-7.4), 200 µL of cells from each well were transferred to black 96-well plates, and GFP fluorescence was measured (excitation=395 nm, bandwidth=9 nm; emission=509 nm, bandwidth=15 nm). Fluorescence intensities were calculated as fluorescence/$OD_{600}$ of the sample minus fluorescence/$OD_{600}$ of a sample of a non-GFP-expressing *E. coli* strain parental to the strain being analyzed in order to correct for both cell density and *E. coli* auto-fluorescence.

2. Vector Construction and Functional Assays 2.1. General Notes.

All vectors used in this study were designed to avoid any antibiotic resistance markers that encode aminoglycoside modifying enzymes (e.g. kanamycin, apramycin, streptomycin resistance markers) or tetracycline because they would interfere with aminoglycoside detection, or the TetR repressor system, respectively. The sequences of all genetic parts amplified from plasmids whose sequences are not publicly available and detailed information on all primers used are provided in each section.

Figure 5:
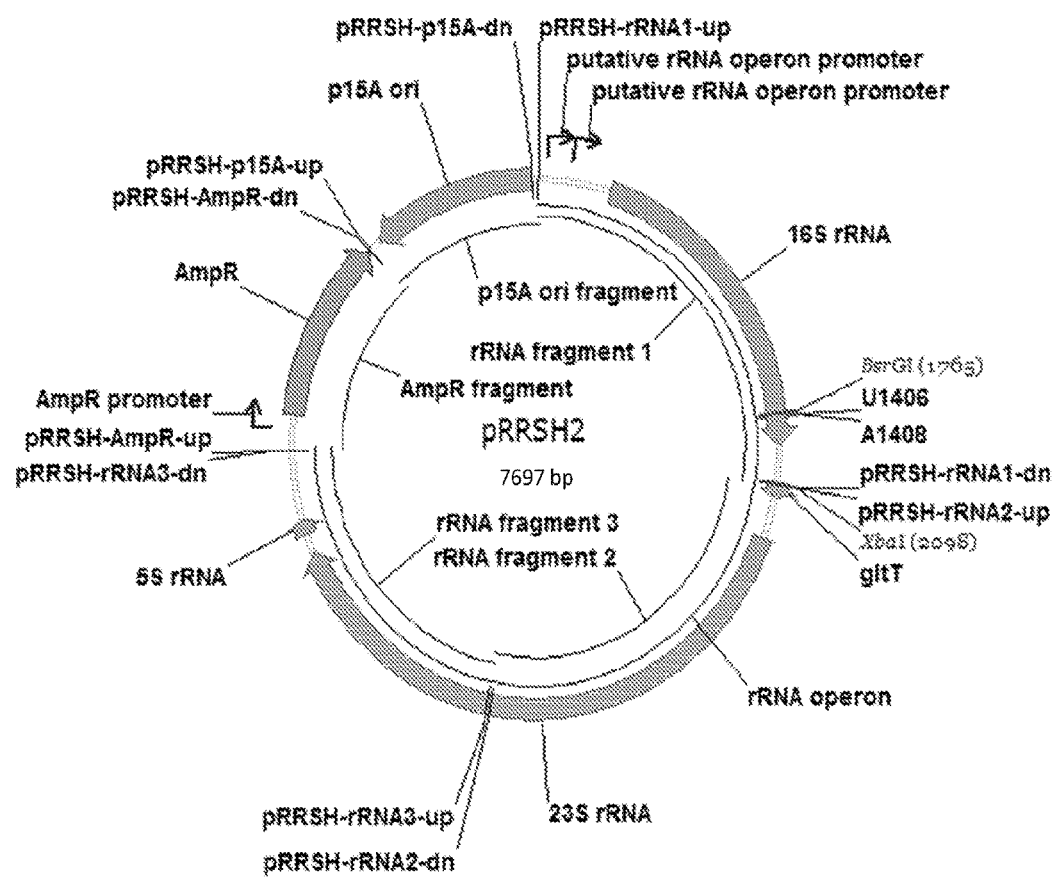
FIG. 5. Plasmid map for pRRSH2.

2.2. rRNA-Expressing Plasmids 2.2.1. Construction of pRRSH2 (FIG. 5).

Plasmid pKK3535 (11.9 kb; Brosius et al., 1981, Plasmid 6:112-118), which contains the constitutively expressed rrnB ribosomal rRNA operon, pMB1 origin of replication, and ampicillin resistance marker, as well as 4.2 kb of non-essential DNA sequence, was used as the starting point for construction of a simplified, refactored rrnB-expressing plasmid pRRSH2 (7.7 kb), which also bears the ampicillin resistance marker, but contains the p15A origin of replication. To construct pRRSH2, concatamerizing overlap extension PCR was used (COE-PCR), a de novo plasmid assembly method that is similar to the CPEC method (Quan et al., 2011, *Nat. Protocols* 6:242-251). In COE-PCR, a circular plasmid is obtained by one pot PCR assembly of linear fragments with short (15-25 bp) overlapping ends followed by transformation of competent *E. coli* with the PCR assembly mixture. The 5.8 kb rrnB operon was amplified as three fragments from pKK3535 using primer pairs pRRSH-rRNA1-up/pRRSH-rRNA1-dn, pRRSH-rRNA2-up/pRRSH-rRNA2-dn, and pRRSH-rRNA3-up/pRRSH-rRNA3-dn. The fragment containing the promoter and coding region of the ampicillin resistance marker was amplified from pKK3535 using primers pRRSH-AmpR-up and pRRSH-AmpR-dn. The fragment containing the p15A origin of replication was amplified from pRepCM3 (Melancon et al., 2009, Bioorg. Med. Chem. Lett. 19:3845-3847) using primers pRRSH-p15A-up and pRRSH-p15A-dn. The resulting five DNA fragments were assembled by COE-PCR and the reaction mixture was concentrated using the Zymo Clean and Concentrator Kit, and introduced into competent *E. coli* DH5α cells. The final pRRSH2 construct was verified by restriction mapping and sequencing. Primer information is provided in Table 1. The priming region of each primer is underlined.

TABLE 1

| primer name | sequence (5'→3') | amplicon size (bp) | template |
|---|---|---|---|
| pRRSH-rRNA1-up | TTTGGTTGAATGTTGCGCGGTC Seq ID No. 1 | 2116 | pKK3535 |
| pRRSH-rRNA1-dn | CGGTGTCCTGGGCCTCTAGAC Seq ID No. 2 | | |
| pRRSH-rRNA2-up | TCTAGAGGCCCAGGACACCGCCCTTTCACGGCGGTAACAG Seq ID No. 3 | 2022 | pKK3535 |
| pRRSH-rRNA2-dn | CTGGTATCTTCGACTGATTTCAGCTCCATCCGCGAGGGACC Seq ID No. 4 | | |

TABLE 1-continued

| primer name | sequence (5'→3') | amplicon size (bp) | template |
|---|---|---|---|
| pRRSH-rRNA3-up | GCTGAAATCAGTCGAAGATACCAGCTGGC Seq ID No. 5 | 1677 | pKK3535 |
| pRRSH-rRNA3-dn | AGCTGCTTTCCTGATGCAAAAACG Seq ID No. 6 | | |
| pRRSH-AmpR-up | CGTTTTTGCATCAGGAAAGCAGCTGATATCAGACGTCAGGTGGCACTTTTC Seq ID No. 7 | 1077 | pKK3535 |
| pRRSH-AmpR-dn | CATATGATCAATCTAAAGTATATATGAGTAAACTTGGTCTGACAG Seq ID No. 8 | | |
| pRRSH-p15A-up | CCAAGTTTACTCATATATACTTTAGATTGATCATATGCTTCGGATCCCTCGAGAGATC Seq ID No. 9 | 934 | pRepCM3 |
| pRRSH-p15A-dn | CCGCGCAACATTCAACCAAAATTACATGTGCGTCAGACCC Seq ID No. 10 | | |

The p15A origin of replication fragment sequence is provided below. Primer binding sites are underlined, and the p15A origin region is shown in bold.

Seq ID No. 11

ATTACATGTG CGTCAGACCC CTTAATAAGA TGATCTTCTT

GAGATCGTTT TGGTCTGCGC GTAATCTCTT GCTCTGAAAA

CGAAAAAACC GCCTTGCAGG GCGGTTTTTC GAAGGTTCTC

TGAGCTACCA ACTCTTTGAA CCGAGGTAAC TGGCTTGGAG

GAGCGCAGTC ACCAAAACTT GTCCTTTCAG TTTAGCCTTA

ACCGGCGCAT GACTTCAAGA CTAACTCCTC TAAATCAATT

ACCAGTGGCT GCTGCCAGTG GTGCTTTTGC ATGTCTTTCC

GGGTTGGACT CAAGACGATA GTTACCGGAT AAGGCGCAGC

GGTCGGACTG AACGGGGGGT TCGTGCATAC AGTCCAGCTT

GGAGCGAACT GCCTACCCGG AACTGAGTGT CAGGCGTGGA

ATTAGACAAA CGCGGCCATA ACAGCGGAAT GACACCGGTA

AACCGAAAGG CAGGAACAGG AGAGCGCACG AGGGAGCCGC

CAGGGGGAAA CGCCTGGTAT CTTTATAGTC CTGTCGGGTT

TCGCCACCAC TGATTTGAGC GTCAGATTTC GTGATGCTTG

TCAGGGGGC GGAGCCTATG GAAAAACGGC TTTGCCGCGG

CCCTCTCACT TCCCTGTTAA GTATCTTCCT GGCATCTTCC

-continued

AGCGGAATAT ATCCTGTATC ACATATTCTG CTGACGCACC

GGTGCAGCCT TTTTTCTCCT GCCACATGAA GCACTTCACT

GACACCCTCA TCAGTGCCAA CATAGTAAGC CAGTATACAC

Figure 6:
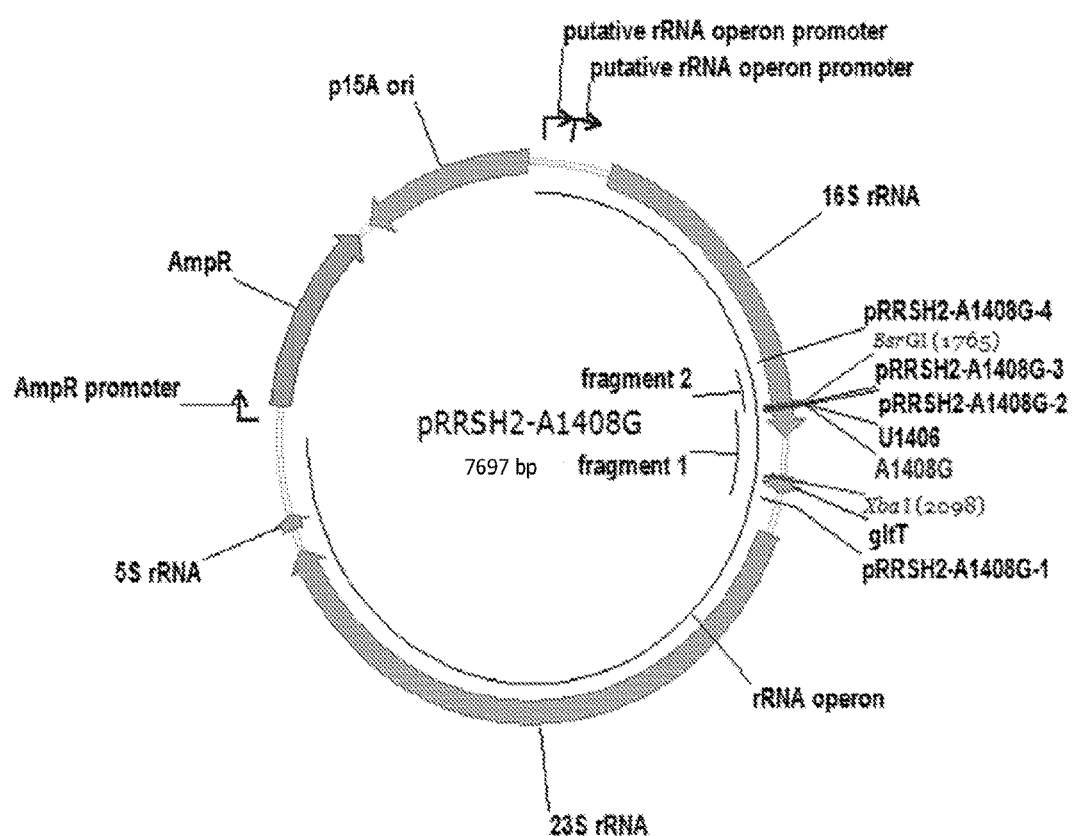
FIG. 6. Plasmid map fop pRRSH2-A1408G.

TCCGCTAGCC CATGGAGATC TCTCGAGGGA TCCGAAG 2.2.2. Construction of pRRSH2-A1408G (FIG. 6) and pRRSH2-U1406A.

Both plasmids were constructed from pRRSH2. A 684 bp region of pRRSH2 containing the 16S rRNA A1408 and U1406 sites was amplified in two fragments with the mutation site at the junction of the fragments. In each case, the two fragments were joined by overlap extension PCR, the resulting PCR product digested with BsrGI and XbaI, and cloned into pRRSH2 digested with the same enzymes. For pRRSH2-A1408G, fragment 1 was amplified using primers pRRSH2-A1408G-1 and pRRSH2-A1408G-2, and fragment 2 was amplified using primers pRRSH2-A1408G-3 and pRRSH2-A1408G-4. For pRRSH2-U1406A, fragment 1 was amplified using primers pRRSH2-A1408G-1 and pRRSH2-U1406A-2, and fragment 2 was amplified using primers pRRSH2-U1406A-3 and pRRSH2-A1408G-4. Introduction of the mutation into each plasmid was verified by sequencing the cloned region of the plasmid containing it. The vector map of pRRSH2-A1408G is given in FIG. 6 as an example. Primer information is provided in Table 2. The priming region of each primer is underlined. The A1408G and U1406A mutation sites are show in bold and double underlined in the primers that contain them.

TABLE 2

| primer name | sequence (5'→3') | amplicon size (bp) | template |
|---|---|---|---|
| pRRSH2-A1408G-1 | TCTCAAACATCACCCGAAGATGAG Seq ID No. 12 | 457 | pRRSH2 |
| pRRSH2-A1408G-2 | CCCGTCGCACCATGGGAGTG Seq ID No. 13 | | |
| pRRSH2-A1408G-3 | CCATGGTGCGACGGGCGGTGTG Seq ID No. 14 | 242 | pRRSH2 |
| pRRSH2-A1408G-4 | GAGGAAGGTGGGGATGACGTC Seq ID No. 15 | | |
| pRRSH2-U1406A-2 | CCCGACACACCATGGGAGTG (used with pRRSH2-A1408G-1) Seq ID No. 16 | 457 | pRRSH2 |
| pRRSH2-U1406A-3 | ACTCCCATGGTGTGTCGGGCGGTG (used with pRRSH2-A1408G-4) Seq ID NO. 17 | 246 | |

-continued

AGGAAATCTC CGCCCCGTTC GTAAGCCATT TCCGCTCGCC

GCAGTCGAAC GACCGAGCGT AGCGAGTCAG TGAGCGAGGA 2.2.3. Functional Verification of pRRSH2-A1408G and pRRSH2 in *E. coli* SQ380.

The ability of pRRSH2-A1408G to confer aminoglycoside resistance was confirmed through a cell viability assay. *E. coli* SQ380 was transformed with pRRSH2-A1408G; and prrnC-sacB was removed by sucrose counterselection, resulting in E. coli SH386. As a control, E. coli SQ380 was also transformed with pRRSH2; and prrnC-sacB was removed by sucrose counterselection, resulting in E. coli SH430. The growth inhibition of these two strains by various kanamycin concentrations was determined by inoculation of each strain (1:100 dilution of a saturated culture) into ten 1 mL wells of a 96-well culture plate containing LB broth with specific concentrations of kanamycin added, growth for 24 hours at 37° C., 200 rpm shaking, and measurement of the $OD_{600}$. The results demonstrated that E. coli SH430, which has no 16S rRNA aminoglycoside resistance mutation, experiences significant growth inhibition at 10 μM kanamycin, and cannot survive at concentrations above 10 μM kanamycin; whereas E. coli SH386, which has the A1408G mutation, shows no growth inhibition at any kanamycin concentration tested, indicating that the mutation confers robust resistance to kanamycin at concentrations as high as 500 μM.

2.3 Sequential Construction of the Reporter Plasmid
2.3.1. General Notes.

The final reporter plasmid, pSH6-KF, was constructed in six steps:

1) construction of pUC19-GFPuv, which contains the gfp-uv gene under control of the PLtetO-1 promoter (see section 2.3.2).

2) optimization of the gfp-uv 5'-untranslated (5'-UTR) region through construction of a five plasmid series pGBSH1-BCD2, pGBSH1-U2, pGBSH1-26.2, pGBSH1-pET, and pGBSH1-pBEST (see section 2.3.3).

3) replacement of the ampicillin resistance marker with a chloramphenicol resistance marker in pGBSH1-BCD2, the plasmid with the highest gfp-uv expression level from Step 2, to give pGBSH3 (see section 2.3.5).

4) insertion of the cassette containing tetR with orthogonal Shine-Dalgarno (O-SD) sequence under control of medium strength promoter BBa_J23016 into pGBSH3 to give pGBSH18 (see section 2.3.6).

5) insertion of the cassette containing the orthogonal 16S rRNA (O-16S) under control of the constitutive lpp promoter to give reporter plasmid pSH3-KF (see section 2.3.7).

6) optimization of the tetR and O-16S promoter strengths for use in E. coli SH386 through construction of an eleven plasmid series pSH4-KF through pSH14-KF (see section 2.4.2).

Figure 7:
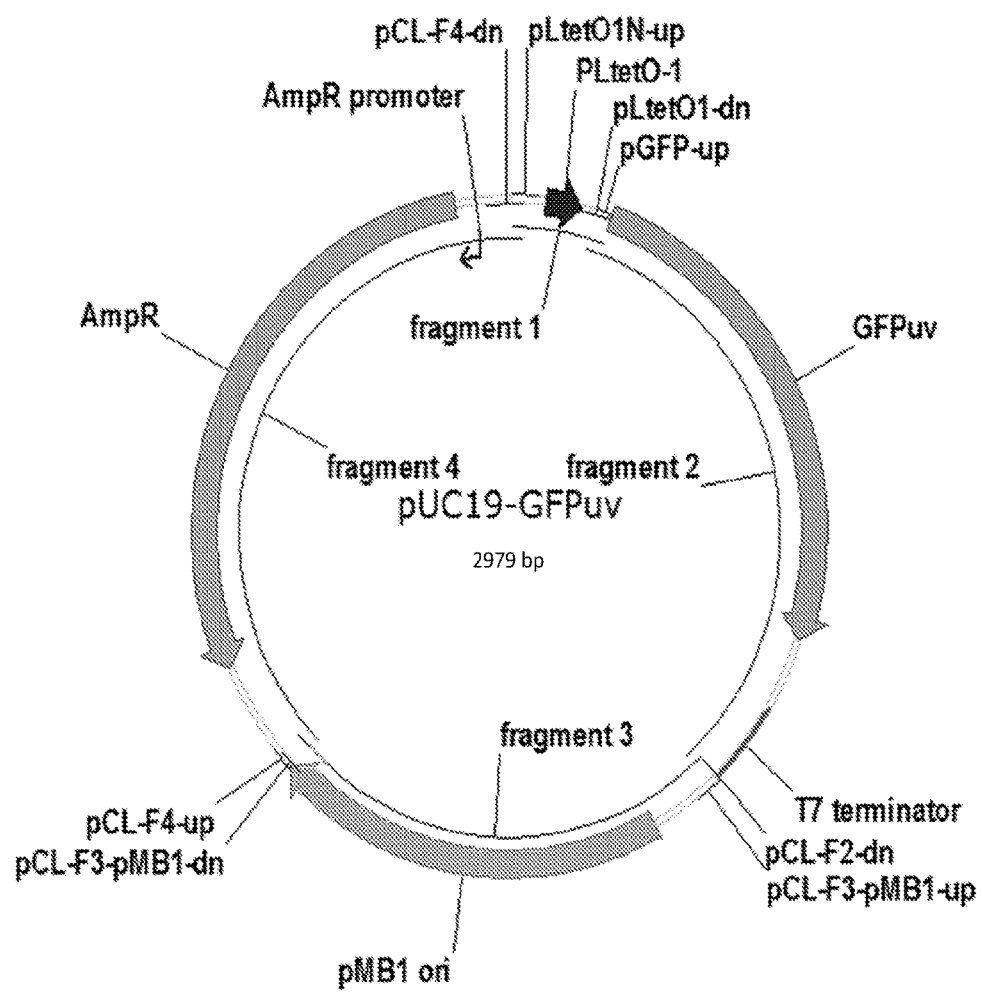
FIG. 7. Plasmid map for pUC19-GFPuv.

2.3.2. Construction and Testing of pUC19-GFPuv (FIG. 7).

This plasmid, which contains the gfp-uv gene under control of the PLtetO-1 promoter/operator (Beck et al., 1982, J. Bacteriol. 150:633-642), pMB1 origin of replication, and ampicillin resistance marker was constructed from four fragments by COE-PCR. The PLtetO-1 promoter/operator was amplified from pSR26_2 (J. Tabor, unpublished) using primers pLTetO1N-up and pLtetO1-dn. The gfp-uv gene was amplified from plasmid pET101-GFP (Young et al., 2010, J. Mol. Biol. 395:361-374) using primers pGFP-up and pCL-F2-dn. The pMB1 origin of replication was amplified from pUC19 using primers pCL-F3-pMB1-up and pCL-F3-pMB1-dn. The ampicillin resistance marker was amplified from pUC19 using primers pCL-F4-up and pCL-F4-dn. All primers are provided in Table 3.

The resulting four fragments were assembled by COE-PCR. The reaction mixture was concentrated using the Zymo Clean and Concentrator Kit, and introduced into competent E. coli DH5α cells. The final construct was verified by restriction mapping and sequencing. The priming region of each primer is underlined.

Figure 8:
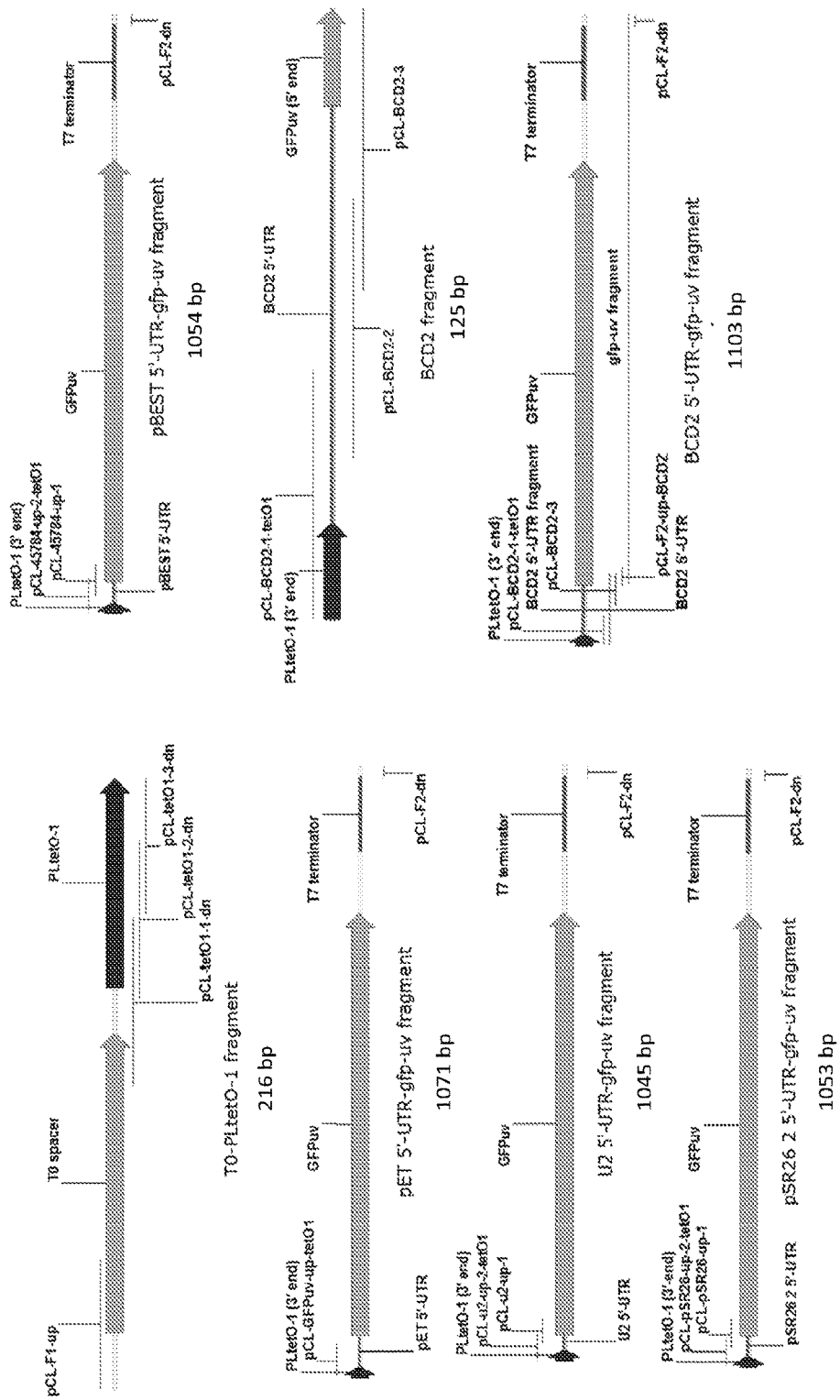
FIG. 8. Maps of T0-PLtetO-1 fragment, pET 5'-UTR-gfp-uv fragment, U2 5'-UTR-gfp-us fragment, pSR26 2 5'-UTR-gfp-uv fragment, pBEST 5'-UTR-gfp-uv fragment, BCD2 fragment, and BCD2 5'-UTR-gfp-uv fragment.

E. coli DH5α transformed with pUC19-GFPuv displayed no fluorescence as determined by plate reader fluorescence assay (see cell density and fluorescence assays section, above, for experimental details). A series of five pUC19-GFPuv derivatives were constructed in which the 5'-UTR was varied (FIG. 8).

TABLE 3

| primer name | sequence (5'→3') | amplicon size (bp) | template |
|---|---|---|---|
| pLtetO1N-up | ACAAACTAGTGCGACCCTGCGTATCACGAGGCCCTTTCGTC Seq ID No. 18 | 159 | pSR26_2 |
| pLtetO1-dn | CATGGTGAAGGGCTCCTGAATTCCTTCATTAATGGTCAGTGCGTCCTGCTGATG Seq ID No. 19 | | |
| pGFP-up | GAAGGAATTCAGGAGCCCTTCACCATG Seq ID No. 20 | 1022 | pET101-GFP |
| pCL-F2-dn | CCGGGCCTCTTGCGGGATATC Seq ID No. 21 | | |
| pCL-F3-pMB1-up | ATATCCCGCAAGAGGCCCGGGCGGTAATAAGCTTACGGTTATCCACAGAATCAGG Seq ID No. 22 | 758 | pUC19 |
| pCL-F3-pMB1-dn | AGACCCCGTCTAGATAGAAAAGATCAAAGGATCTTCTTGAG Seq ID No. 23 | | |
| pCL-F4-up | CTTTGATCTTTTCTATCTAGACGGGGTCTGACGCTCAGTG Seq ID No. 24 | 1137 | pUC19 |
| pCL-F4-dn | GCAGGGTCGCACTAGTTTGTTTATTTTTCTAAATACATTCAAATATGTATCCGCTC Seq ID No. 25 | | |

The gfp-uv fragment sequence is provided below. Primer binding sites are underlined, the gfp-uv coding region is shown in bold with start and stop codons underlined, and the T7 terminator sequence is double underlined.

```
                                             Seq ID No. 26
GAAGGAATTC AGGAGCCCTT CACCATGAGT AAAGGAGAAG

AACTTTTCAC TGGAGTTGTC CCAATTCTTG

TTGAATTAGA TGGTGATGTT AATGGGCACA AATTTTCTGT

CAGTGGAGAG GGTGAAGGTG ATGCAACATA

CGGAAAACTT ACCCTTAAAT TTATTTGCAC TACTGGAAAA

CTACCTGTTC CATGGCCAAC ACTTGTCACT

ACTTTCTCTT ATGGTGTTCA ATGCTTTTCC CGTTATCCGG

ATCACATGAA ACGGCATGAC TTTTTCAAGA

GTGCCATGCC CGAAGGTTAT GTACAGGAAC GCACTATATC
```

-continued

```
TTTCAAAGAT GACGGGAACT ACAAGACGCG

TGCTGAAGTC AAGTTTGAAG GTGATACCCT TGTTAATCGT

ATCGAGTTAA AAGGTATTGA TTTTAAAGAA

GATGGAAACA TTCTCGGACA CAAACTCGAA TACAACTATA

ACTCACACAA TGTATACATC ACGGCAGACA

AACAAAAGAA TGGAATCAAA GCTAACTTCA AAATTCGCCA

CAACATTGAA GATGGATCCG TTCAACTAGC

AGACCATTAT CAACAAAATA CTCCAATTGG CGATGGCCCT

GTCCTTTTAC CAGACAACCA TTACCTGTCG

ACACAATCTG CCCTTTCGAA AGATCCCAAC GAAAAGCGTG

ACCACATGGT CCTTCTTGAG TTTGTAACTG

CTGCTGGGAT TACACATGGC ATGGATGAGC TCTACAAACT

CGAGCACCAC CACCACCACC ACTGAAAGGG

CGAGCTCAAT TCGAAGCTTG AAGGTAAGCC TATCCCTAAC

CCTCTCCTCG GTCTCGATTC TACGCGTACC

GGTCATCATC ACCATCACCA TTGAGTTTGA TCCGGCTGCT

AACAAAGCCC GAAAGGAAGC TGAGTTGGCT

GCTGCCACCG CTGAGCAATA ACTAGCATAA CCCCTTGGGG

CCTCTAAACG GGTCTTGAGG GGTTTTTTGC

TGAAAGGAGG AACTATATCC GGATATCCCG CAAGAGGCCC GG
```

Figure 9:
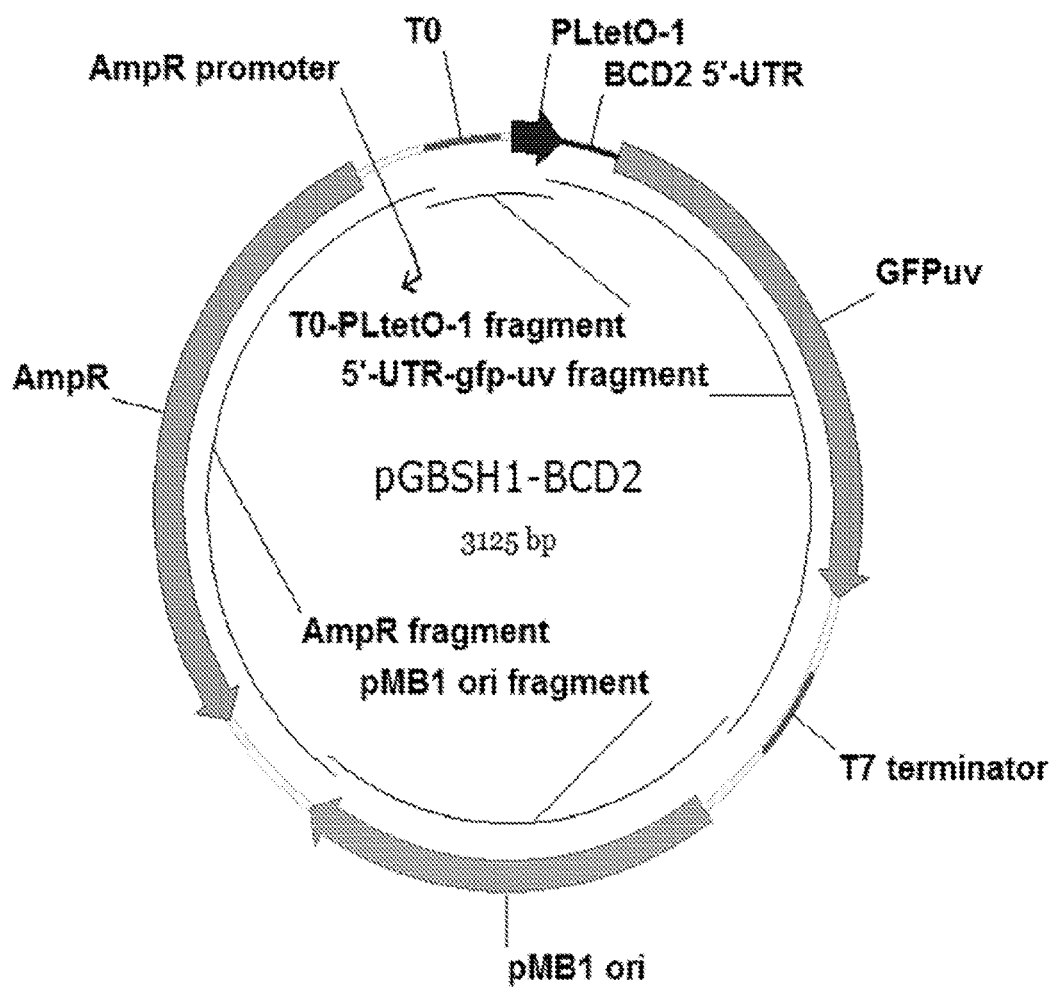
FIG. 9. Plasmid map for pGBSH1-BCD2.

2.3.3. Construction of the pGBSH1 Plasmid Series (FIG. 8 and FIG. 9)

The pGBSH1 plasmid series was constructed by replacement of the gfp-uv 5'-UTR on pUC19-GFPuv with 5 different 5'-UTRs. The 5'-UTRs included three 5'-UTRs that were reported to be strong [BCD2 (Mutilak et al., 2013, *Nat. Methods* 10:354-360), U2 (Mutilak et al., 2013, *Nat. Methods* 10:347-353), pBEST (cat. no. #45784, Addgene, Cambridge, Mass.)] and two representing the intact 5'-UTRs associated with the GFPuv gene in pET101-GFP (pET) and the PLtetO-1 promoter in pSR26_2 (26.2). Additionally, a T0 spacer sequence was added between the ampicillin resistance gene and the PLtetO-1 portion to attempt to minimize any polar effects on GFP expression. The T0 spacer was appended to the 5' end of the PLtetO-1 fragment. Construction of these plasmids was accomplished by five COE-PCR reactions, each employing four fragments, three of which (pMB1 origin, ampicillin resistance marker, T0 spacer-PLtetO-1) were identical in all five reactions, and one (the 5'-UTR-gfp-uv fragment) of which was variable. The fragments containing the pMB1 origin and ampicillin resistance marker were identical to those used in construction of pUC19-GFPuv.

The T0 spacer-PLtetO-1 fragment was constructed by three sequential PCR reactions in which the product of the previous reaction was used as the template for the next reaction. The T0 spacer was amplified from plasmid pSR26_2 using primers pCL-F1-up and pCL-tetO1-dn-1. The resulting PCR product was used as the template for a second round of PCR using primers pCL-F1-up and pCL-tetO1-dn-2. The resulting PCR product was used as the template for a third round of PCR using primers pCL-F1-up and pCL-tetO1-dn-3 to generate the final fragment.

The five 5'-UTR-gfp-uv fragments (FIG. 8) were constructed as follows: The pET 5'-UTR-gfp-uv fragment was constructed in a single PCR reaction by amplification from plasmid pET101-GFP using primers pCL-GFPuv-up-tetO1 and pCL-F2-dn. The U2 5'-UTR-gfp-uv, 26.2 5'-UTR-gfp-uv, and pBEST 5'-UTR-gfp-uv fragments were each constructed by two sequential PCR reactions in which the product of the first reaction (the gfp-uv-containing fragment, which was amplified from plasmid pET101-GFP), was used as the template for the second reaction. The U2 5'-UTR-gfp-uv fragment was constructed by amplification using primers pCL-u2-up-1 and pCL-F2-dn; and the resulting PCR product used as the template for a second round of PCR using primers pCL-u2-up-2-tetO1 and pCL-F2-dn. The 26.2 5'-UTR-gfp-uv fragment was constructed by amplification using primers pCL-pSR26-up-1 and pCL-F2-dn; and the resulting PCR product used as the template for a second round of PCR using primers pCL-pSR26-up-2-tetO1 and pCL-F2-dn. The pBEST 5'-UTR-gfp-uv fragment was constructed by amplification using primers pCL-45784-up-1 and pCL-F2-dn; and the resulting PCR product used as the template for a second round of PCR using primers pCL-45784-up-2-tetO1 and pCL-F2-dn. The BCD2 5'-UTR was constructed as a stand-alone fragment by templateless assembly using three primers (pCL-BCD2-1-tetO1, pCL-BCD2-2, and pCL-BCD2-3). A gfp-uv-containing fragment was amplified from pET101-GFP using primers pCL-F2-up-BCD2 and pCL-F2-dn; and the BCD2 5'-UTR and gfp-uv-containing fragments were joined by overlap extension PCR and amplified using outside primers pCL-BCD2-1-tetO1 and pCL-F2-dn to generate the final BCD2 5'-UTR-gfp-uv fragment.

Each of the five 5'-UTR-gfp-uv fragment variants was then assembled with the T0 spacer-PLtetO-1, pMB1 origin, and ampicillin resistance marker fragments in a COE-PCR reaction. Each reaction mixture was concentrated using the Zymo Clean and Concentrator Kit and introduced into competent *E. coli* DH5α cells. Each final construct was verified by restriction mapping and sequencing. Primer information is provided in Table 4. The priming region of each primer is underlined. The vector map of pGBSH1-BCD2 is given as an example in FIG. 9.

The 5'-UTRs examined are provided in Table 5.

TABLE 4

| primer name | sequence (5'→3') | amplicon size (bp) | template |
| --- | --- | --- | --- |
| pCL-F1-up | ACAAACTAGTGCGACCCTGCTGCTTGGATTCTCACCAATAAAAAAC Seq ID NO. 27 | 167 | pSR26_2 |
| pCL-tetO1-dn-1 | TGTCAATCTCTATCACTGATAGGGATTTGATATCGAGCTCGCTTGGACTCCTGTTGATAG Seq ID NO. 28 | | |

TABLE 4-continued

| primer name | sequence (5'→3') | amplicon size (bp) | template |
|---|---|---|---|
| pCL-tetO1-dn-2 | GCTCAGTATCTCTATCACTGATAGGGATGTCAATCTCTATCACTGATAGGGATTTG Seq ID No. 29 | 194 | PCR pdt. |
| pCL-tetO1-dn-3 | GGTCAGTGCGTCCTGCTGATGTGCTCAGTATCTCTATCACTGATAGGG Seq ID NO. 30 | 216 | PCR pdt. |
| pCL-GFPuv-up-tetO1 pCL-F2-dn | ATCAGCAGGACGCACTGACCCCTCTAGAAATAATTTTGTTTAACTTTAAGAAGGAATTC Seq ID No. 31 CCGGGCCTCTTGCGGGATATC (same is used to construct pUC19-GFPuv) Seq ID NO. 32 | 1071 | pET101-GFP |
| pCL-u2-up-1 | AAAGAGGAGAAAGGTACCATGAGTAAAGGAGAAGAACTTTTCACTGG (used with pCL-F2-dn) Seq ID NO. 33 | 1016 | pET101-GFP |
| pCL-u2-up-2-tetO1 | ATCAGCAGGACGCACTGACCGAATTCATTAAAGAGGAGAAAGGTACCATGAG (used with pCL-F2-dn) Seq ID NO. 34 | 1045 | PCR pdt. |
| pCL-pSR26-up-1 | AGCAAAGCCCAATTTTAAACAAATGAGTAAAGGAGAAGAACTTTTCACTGG (used with pCL-F2-dn) Seq ID NO. 35 | 1020 | pET101-GFP |
| pCL-pSR26-up-2-tetO1 | ATCAGCAGGACGCACTGACCGCATAAAGGACTTAGCAAAGCCCAATTTTAAAC (used with pCL-F2-dn) Seq ID NO. 36 | 1053 | PCR pdt. |
| pCL-45784-up-1 | ATTTTGTTTAACTTTAAGAAGGATCCATGAGTAAAGGAGAAGAACTTTTCACTGG (used with pCL-F2-dn) Seq ID NO. 37 | 1024 | pET101-GFP |
| pCL-45784-up-2-tetO1 | ATCAGCAGGACGCACTGACCGCTAGCAATAATTTTGTTTAACTTTAAGAAGGATCCATG (used with pCL-F2-dn) Seq ID No. 38 | 1054 | PCR pdt. |
| pCL-BCD2-1-tetO1 | ATCAGCAGGACGCACTGACCGGGCCCAAGTTCACTTAAAAAGGAGATCAAC Seq ID NO. 39 | | |
| pCL-BCD2-2 | GATTAAGATGTTTCAGTACGAAAATTGCTTTCATTGTTGATCTCCTTTTTAAG Seq ID No. 40 | 125 | primer assembly |
| pCL-BCD2-3 | AGTTCTTCTCCTTTACTCATTAGAAAACCTCCTTAGCATGATTAAGATGTTTCAGTAC Seq ID No. 41 | | |
| pCL-F2-up-BCD2 | ATGAGTAAAGGAGAAGAACTTTTCACTGGAG (used with pCL-F2-dn) Seq ID NO. 42 | 998 | pET101-GFP |

The T0 spacer fragment sequence is provided below. Primer binding sites are underlined, and the T0 spacer region is shown in italics.

Seq ID No. 43
TGCTTGGATT CTCACCAATA AAAAACGCCC *GGCGGCAACC*

*GAGCGTTCTG AACAAATCCA GATGGAGTTC*

*TGAGGTCATT ACTGGAT*CTA TCAACAGGAG TCCAAGCGAG

CTCGATATCA AAT 2.3.4. pGBSH1 Series Functional Assay.

E. coli DH5α transformed with pGBSH1-BCD2, pGBSH1-U2, pGBSH1-26.2, pGBSH1-pET, and pGBSH1-pBEST displayed a range of fluorescences (FIG. 10) as determined by plate reader fluorescence assays (see cell density and fluorescence assays section, above, for experimental details), with pGBSH1-BCD2 resulting in the highest fluorescence. Thus, pGBSH1-BCD2 was selected for further development.

Figure 11:
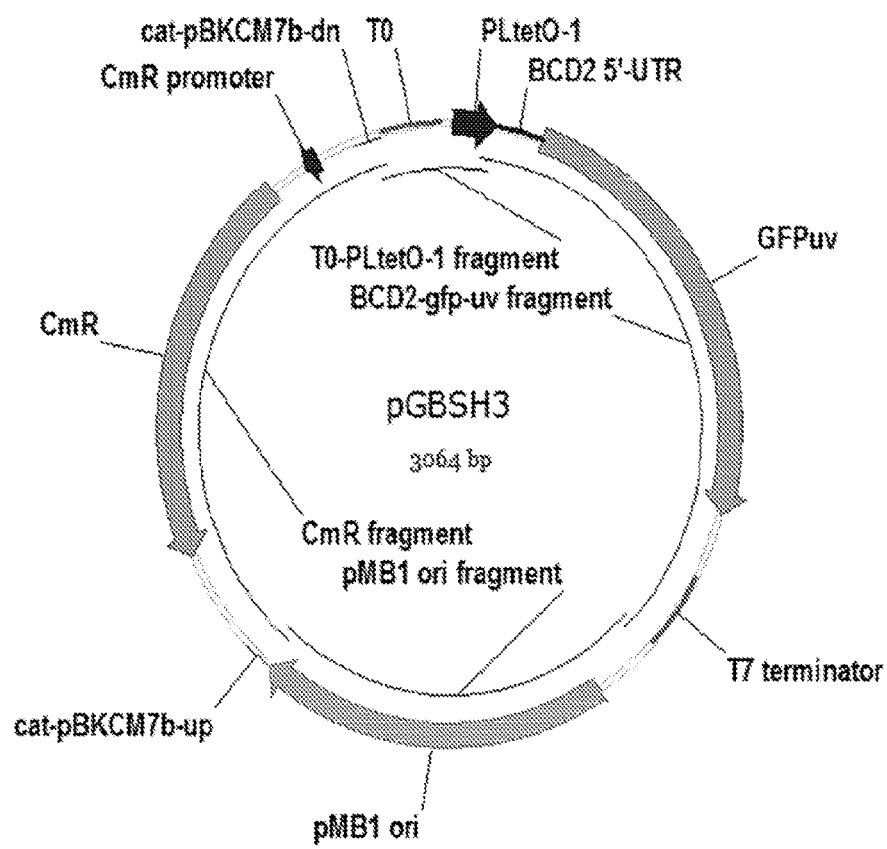
FIG. 11. Plasmid map for pGBSH3.

2.3.5. Construction and Testing of pGBSH3 (FIG. 11)

After identification of plasmid pGBSH1-BCD2 as the variant resulting in the highest fluorescence, the ampicillin resistance marker in pGBSH1-BCD2 was replaced with a chloramphenicol resistance marker so that the resulting plasmid, pGBSH3, could be co-transformed with pRRSH2-A1408G. A four fragment COE-PCR reaction was employed to construct pGBSH3. Three of the fragments (BCD2 5'-UTR-gfp-uv, pMB1 origin, and T0-PLtetO-1) were identical to those used to construct pGBSH1-BCD2. The fragment containing the chloramphenicol resistance marker was

TABLE 5

| 5'-UTR | Sequence | length (bp) |
|---|---|---|
| pET | CCTCTAGAAATAATTTTGTTTAACTTTAAGAAGGAATTCAGGAGCCCTTCACC Seq ID No. 44 | 53 |
| U2 | GAATTCATTAAAGAGGAGAAAGGTACC Seq ID No. 45 | 27 |
| 26_2 | GCATAAAGGACTTAGCAAAGCCCAATTTTAAACAA Seq ID No. 46 | 35 |
| pBEST | GCTAGCAATAATTTTGTTTAACTTTAAGAAGGATCC Seq ID No.47 | 36 |
| BCD2 | GGGCCCAAGTTCACTTAAAAAGGAGATCAACAATGAAAGCAATTTTCGTACTGAAACATCTTAATCATGCTAAGGAGGTTTTCTA Seq ID No. 48 | 85 | amplified from plasmid pBKCM7b (Charles E. Melancon III, unpublished) using primers cat-pBKCM7b-up and cat-pBKCM7b-dn. After COE-PCR, concentration using a Zymo Clean and Concentrator Kit, and transformation, the final construct was verified by restriction mapping and sequencing. Primer information is provided in Table 6. The priming region of each primer is underlined. Retention of robust fluorescence by *E. coli* DH5α cells transformed with pGBSH3 was verified by plate reader fluorescence assays (FIG. 2B) (see cell density and fluorescence assays section, above, for experimental details).

TABLE 6

| primer name | sequence (5'→3') | amplicon size (bp) | template |
|---|---|---|---|
| cat-pBKCM7b-up | CTTTTCTATCTAGACGGGGTCT<u>TTTGATAGAAAATCATAAAAGGATTTGC</u><br>Seq ID No. 49 | 1069 | pBKCM7b |
| cat-pBKCM7b-dn | GCAGGGTCGCACTAGTTTGT<u>GGATCCAACTGCATTCAGAATAAATAAATC</u><br>Seq ID No. 50 | | |

The chloramphenicol resistance marker fragment sequence is provided below. Primer binding sites are underlined, the promoter sequence is double underlined, and the chloramphenicol acetyltransferase coding region is shown in bold with start and stop codons underlined.

Seq ID No. 51

<u>GGATCCAACT GCATTCAGAA TAAATAAATC</u> CTGGTGTCCC

TGTTGATACC GGGAAGCCCT GGGCCAACTT

TTGGCGAAAA TGAGACGTTG ATCGGCACG<u>T AAGAGGTTCC</u>

<u>AACTTTCACC ATAATGAAAT</u> AAGATCACTA

CCGGGCGTAT TTTTTGAGTT GTCGAGATTT TCAGGAGCTA

AGGAAGCTAA AATGGAGAAA AAAATCACTG

GATATACCAC CGTTGATATA TCCCAATGGC ATCGTAAAGA

ACATTTTGAG GCATTTCAGT CAGTTGCTCA

ATGTACCTAT AACCAGACCG TTCAGCTGGA TATTACGGCC

TTTTTAAAGA CCGTAAAGAA AAATAAGCAC

AAGTTTTATC CGGCCTTTAT TCACATTCTT GCCCGCCTGA

TGAATGCTCA TCCGGAATTA CGTATGGCAA

TGAAAGACGG TGAGCTGGTG ATATGGGATA GTGTTCACCC

TTGTTACACC GTTTTCCATG AGCAAACTGA

AACGTTTTCA TCGCTCTGGA GTGAATACCA CGACGATTTC

CGGCAGTTTC TACACATATA TTCGCAAGAT

GTGGCGTGTT ACGGTGAAAA CCTGGCCTAT TTCCCTAAAG

GGTTTATTGA GAATATGTTT TTCGTCTCAG

CCAATCCCTG GGTGAGTTTC ACCAGTTTTG ATTTAAACGT

GGCCAATATG GACAACTTCT TCGCCCCCGT

TTTCACCATG GGCAAATATT ATACGCAAGG CGACAAGGTG

CTGATGCCGC TGGCGATTCA GGTTCATCAT

AGAATGAAAA GAAACAGATA GATTTTTTAG

TTCTTTAGGC CCGTAGTCT<u>G CAAATCCTTT TATGATTTTC</u>

<u>TATCAAA</u>

Figure 13:
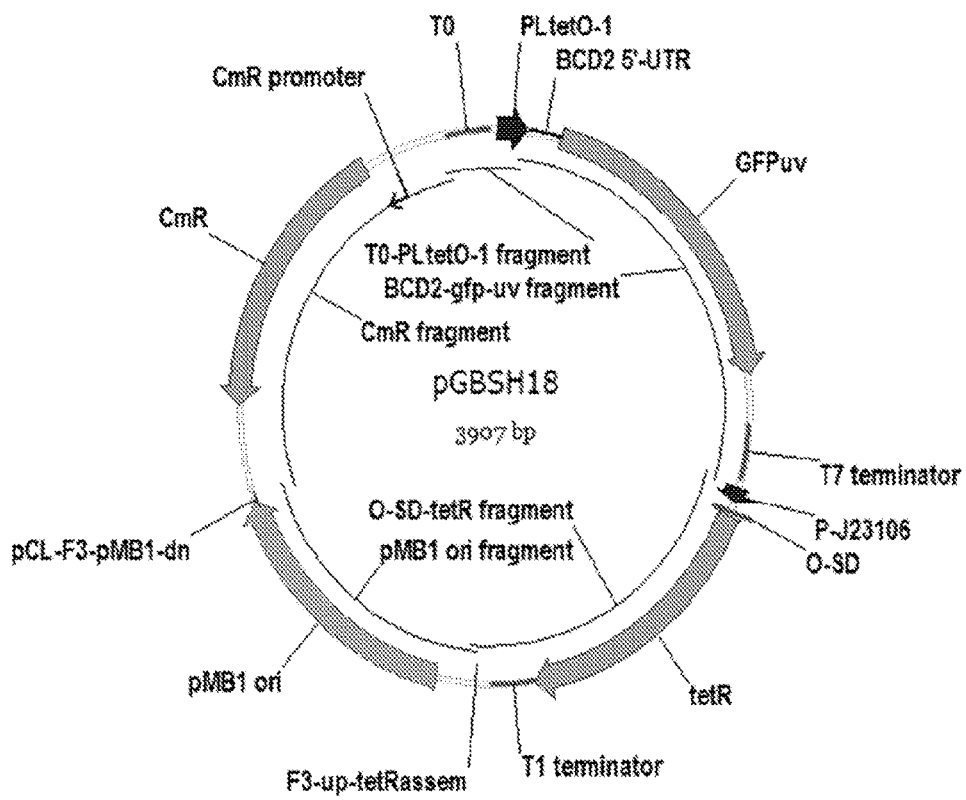
FIG. 13. Plasmid map for pGBSH18.
Figure 14:
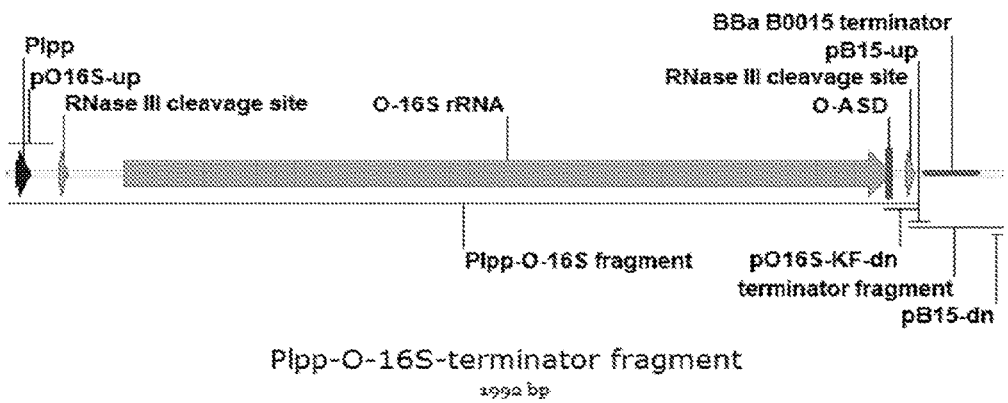
FIG. 14. Map of Plpp-O-16S-terminator fragment.

2.3.6. Construction and Testing of pGBSH18 (FIG. 13)

A cassette containing the tetR gene with orthogonal Shine-Dalgarno (O-SD) sequence ATCCC (Lee et al., 1996 RNA 2:1270-1285; Abdi et al., 2007, *RNA* 11: 1624-1632) under control of medium strength promoter BBa_J23106 (J. Christopher Anderson, unpublished) and containing the T1 terminator was inserted into pGBSH3 to generate pGBSH18. A five fragment COE-PCR reaction was employed to construct pGBSH18. Three of the fragments (the BCD2 5'-UTR-gfp-uv, chloramphenicol resistance marker, and T0-PLtetO-1) were identical to those used to construct pGBSH1-BCD2 and pGBSH3. The pMB1 origin was amplified from pGBSH3 using primers F3-up-tetRassem and pCL-F3-pMB1-dn.

Figure 12:
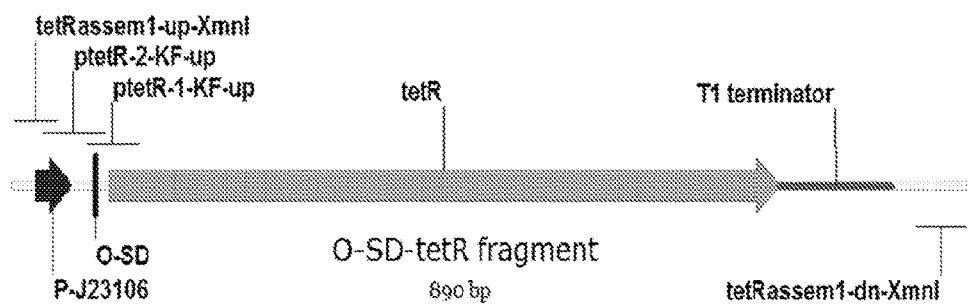
FIG. 12. Map of O-SD-tetR fragment.

The fragment containing O-SD-tetR (FIG. 12) was constructed by three sequential PCR reactions in which the product of the previous reaction was used as the template for the next reaction. The tetR gene with T1 terminator was amplified from pSR26_2 using primers ptetR-1-KF-up and tetRassem1-dn-XmnI. The resulting PCR product was used as the template for a second round of PCR using primers ptetR-2-KF-up and tetRassem1-dn-XmnI. The resulting PCR product was used as the template for a third round of PCR using primers tetRassem1-up-XmnI and tetRassem1-dn-XmnI to generate the final fragment. After COE-PCR, concentration using a Zymo Clean and Concentrator Kit, and transformation, the final construct was verified by restriction mapping and sequencing. Primer information is provided in Table 7. The priming region of each primer is underlined. The O-SD sequence and ATG start codon are shown in bold and are double underlined in the primers that contain them.

TABLE 7

| primer name | sequence (5'→3') | amplicon size (bp) | template |
| --- | --- | --- | --- |
| F3-up-tetRassem pCL-F3-pMB1-dn | GCGGTAATAAGCTTACGGTTATCCAC Seq ID NO. 52 AGACCCCGTCTAGATAGAAAAGATCAAAGGATCTTCTTGAG (same as used to construct pUC19-GFPuv) Seq ID No. 53 | 738 | pGBSH3 |
| ptetR-1-KF-up | ACAATCGATA<u>CATCCCCCGCAAATGATGTCTCGTTTAGATAAAAGTAA</u> AG Seq ID No. 54 | 823 | pSR26_2 |
| tetRassem1-dn-Xmn1 | TGTGGATAACCGTAAGCTTATTACCG<u>CTTTGAGTGAGCTGATACCGC</u> Seq ID No. 55 | | |
| ptetR-2-KF-up | CTAGCTCAGTCCTAGGTATAGTGCTAGCCCAGCCAGAGAA<u>ACAATCGA TACATCCCCC</u> Seq ID NO. 56 | 863 | PCR pdt. |
| tetRassem1-up-Xmn1 | ATATCCCGCAAGAGGCCCGGTTTACGG<u>CTAGCTCAGTCCTAG</u> Seq ID NO. 57 | 890 | PCR pdt. |

The sequence of the tetR-T1 terminator fragment is provided below. Primer binding sites are underlined, the tetR coding sequence is shown in bold, and the T1 terminator region is double underlined.

Seq ID No. 58

<u>ATGATGTCTC GTTTAGATAA AAGTAAAGTG ATTAACAGCG</u>

CATTAGAGCT GCTTAATGAG GTCGGAATCG

AAGGTTTAAC AACCCGTAAA CTCGCCCAGA AGCTAGGTGT

AGAGCAGCCT ACATTGTATT GGCATGTAAA

AAATAAGCGG GCTTTGCTCG ACGCCTTAGC CATTGAGATG

TTAGATAGGC ACCATACTCA CTTTTGCCCT

TTAGAAGGGG AAAGCTGGCA AGATTTTTTA CGTAATAACG

CTAAAAGTTT TAGATGTGCT TTACTAAGTC

ATCGCGATGG AGCAAAAGTA CATTTAGGTA CACGGCCTAC

AGAAAAACAG TATGAAACTC TCGAAAATCA

ATTAGCCTTT TTATGCCAAC AAGGTTTTTC ACTAGAGAAT

GCATTATATG CACTCAGCGC AGTGGGGCAT

TTTACTTTAG GTTGCGTATT GGAAGATCAA GAGCATCAAG

TCGCTAAAGA AGAAAGGGAA ACACCTACTA

CTGATAGTAT GCCGCCATTA TTACGACAAG CTATCGAATT

ATTTGATCAC CAAGGTGCAG AGCCAGCCTT

CTTATTCGGC CTTGAATTGA TCATATGCGG ATTAGAAAAA

CAACTTAAAT GTGAAAGTGG GTCTTAA<u>GGC</u>

<u>ATCAAATAAA ACGAAAGGCT CAGTCGAAAG ACTGGGCCTT</u>

<u>TCGTTTTATC TGTTGTTTGT CGGTGAACGC</u>

<u>TCTCCTGAGT AGGACAAATC CGCCGCCCTA GA</u>CCTAGGCG

TTCGGCTGCG GCGA<u>GCGGTA TCAGCTCACT</u>

<u>CAAAG</u>

The sequence of the pMB1 origin in pGBSH18 is provided below with spontaneous mutations shown underlined and in bold. G at position 107 was mutated to C, and G at position 457 was mutated to A.

Seq ID No. 59

CGCGTTGCTG GCGTTTTTCC ATAGGCTCCG CCCCCCTGAC

GAGCATCACA AAAATCGACG CTCAAGTCAG

AGGTGGCGAA ACCCGACAGG ACTATAAAGA TACCAG<u>C</u>CGT

TTCCCCCTGG AAGCTCCCTC GTGCGCTCTC

CTGTTCCGAC CCTGCCGCTT ACCGGATACC TGTCCGCCTT

TCTCCCTTCG GGAAGCGTGG CGCTTTCTCA

TAGCTCACGC TGTAGGTATC TCAGTTCGGT GTAGGTCGTT

CGCTCCAAGC TGGGCTGTGT GCACGAACCC

CCCGTTCAGC CCGACCGCTG CGCCTTATCC GGTAACTATC

GTCTTGAGTC CAACCCGGTA AGACACGACT

TATCGCCACT GGCAGCAGCC ACTGGTAACA GGATTAGCAG

AGCGAGGTAT GTAGGCGGTG CTACAGAGTT

CTTGAAGTGG TGGCCTAACT ACGGCTACAC TAGAAG<u>A</u>ACA

GTATTTGGTA TCTGCGCTCT GCTGAAGCCA

GTTACCTTCG GAAAAGAGT TGGTAGCTCT TGATCCGGCA

AACAAACCAC CGCTGGTAGC GGTGGTTTTT

TTGTTTGCAA GCAGCAGATT ACGCGCAGAA AAAAGGATC

TCAAGAAGAT CCTTT

Retention of robust fluorescence by *E. coli* cells DH5α transformed with pGBSH18 was verified as by plate reader fluorescence assays (FIG. 2B) (see cell density and fluorescence assays section, above, for experimental details). During the sequencing process, two spontaneous mutations in the pMB1 origin (see below for locations) were discovered. It is unclear whether these mutations have any effect on plasmid copy number, but it is clear from fluorescence assays that they do not interfere with replication in *E. coli* DH5α or gfp-uv expression.

Figure 15:
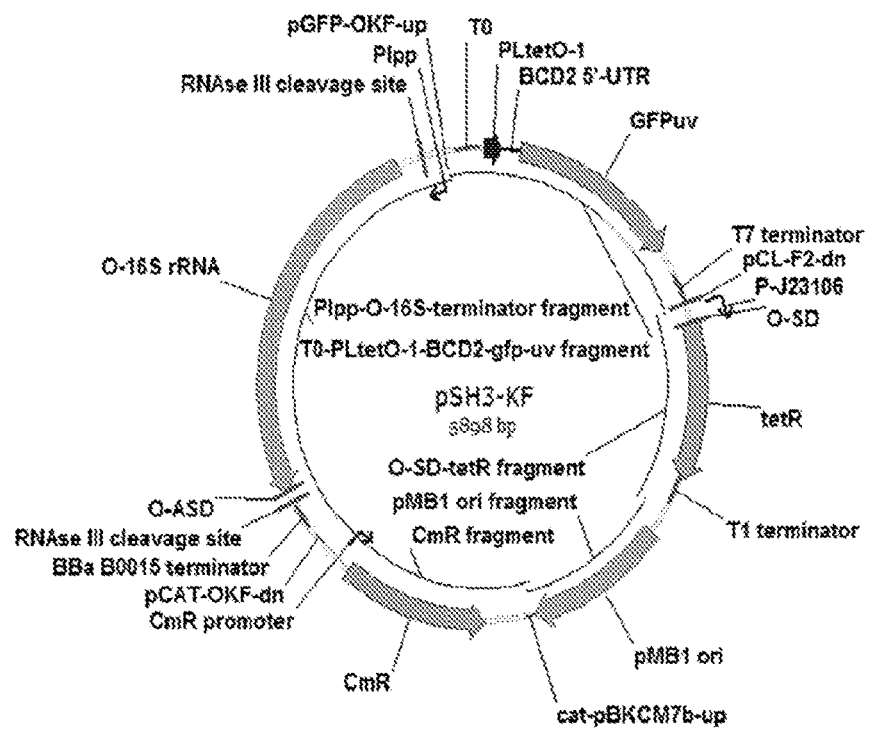
FIG. 15. Plasmid map for pSH3-KF.

2.3.7. Construction and Testing of pSH3-KF (FIG. 15) in *E. coli* DH5α.

A cassette containing the orthogonal 16S rRNA (O-16S) with orthogonal anti-Shine-Dalgarno (O-ASD) sequence TGGGG (Lee et al., 1996 RNA 2:1270-1285; Abdi et al., 2007, *RNA* 11:1624-1632) was inserted into pGBSH18 to generate pSH3-KF, which contains all the components of the orthogonal ribosome-based fluorescent reporter. A five fragment COE-PCR reaction was employed to construct pSH3-KF.

Two of the fragments (the O-SD-tetR and pMB1 origin) were identical to those used to construct pGBSH18. The chloramphenicol resistance marker fragment was amplified from pBGSH18 using primers cat-pBKCM7b-up and pCAT-OKF-dn. A fragment containing T0-PLtetO-1 and BCD2 5'-UTR-gfp-uv was also amplified from pGBSH18 using primers pGFP-OKF-up and pCL-F2-dn.

The fragment containing the orthogonal 16S rRNA (O-16S) under control of the reportedly strong lpp promoter (Plpp; Inouye et al., 1985, *Nucleic Acids Res.* 1985, 13, 13:3101-3110) was constructed by amplifying the Plpp-16S rRNA cassette from plasmid pTrcSS1d-rrsBb (Shinichiro Shoji, unpublished) using upstream primer pO16S-up and mutagenic downstream primer pO16S-KF-dn which was used to install the orthogonal anti-Shine-Dalgarno (O-ASD) sequence. The strong terminator BBa_B0015 (Chen et al., 2013, *Nat. Methods* 10:659-664) was amplified from plasmid pSR26_2 using primers pB15-up and pB15-dn and appended to the 3' end of the Plpp-O-16S fragment by overlap extension PCR to attempt to minimize any polar effects on other genes in the construct. After COE-PCR, concentration using a Zymo Clean and Concentrator Kit, and transformation, the final construct was verified by restriction mapping and sequencing. Primer information is provided in Table 8. The priming region of each primer is underlined. The lpp promoter and O-ASD sequences are shown in bold in the primers that contain them.

TABLE 8

| primer name | sequence (5'-3') | amplicon size (bp) | template |
|---|---|---|---|
| pGFP-OKF-up | GAATTCGTGGCCCTGCATGCA CAAACTAGTGCGACCCTGCTGC Seq ID No. 60 | 1319 | pG6SH18 |

TABLE 8 -continued

| primer name | sequence (5'-3') | amplicon size (bp) | template |
|---|---|---|---|
| pCL-F2-dn | CCGGGCCTCTTGCGGGATATC (same is used to construct pUC19-GFPuv) Seq ID NO. 61 | | |
| cat-pBKCM7b-up | CTTTTCTATCTAGACGGGGTCT TTTGATAGAAAATCATAAAAGG ATTTGC (same as used to construct pG6SH3) Seq ID NO. 62 | 1091 | pG6SH18 |
| pCAT-OKF-dn | GTACCCGTGGATCCTCTAGAGG ATCCAACTGCATTCAGAATAAA TAAATC Seq ID NO. 63 | | |
| pO16S-up | GCATGCAGGGCCACGAATTCTC AACATAAAAAACTTTGTGTAAT ACTTGTAACGCTAGATCCGGTA GCGATCGAAAGCGAAGCGGCAC Seq ID No. 64 | 1824 | pTrcSS1d-rrsBb |
| pO16S-KF-dn | CTGCAGTATCAGACAATCTGTG TGAGCACTACAAAGTACGCTTC TTTAAGGTACCCCATGATCCA ACCG Seq ID No. 65 | | |
| pB15-up | CAGATTGTCTGATACTGCAGGC ATGATAATAATCTAGACCAGG Seq ID No. 66 | 188 | pSR26_2 |
| pB15-dn | TCTAGAGGATCCACGGGTACC Seq ID No. 67 | | |

The sequence of the lpp promoter—O16S fragment is provided below. Primer binding sites are underlined, the lpp promoter is shown in italics and underlined, the O-16S rRNA coding region is shown in old, and the O-ASD sequence is double underlined.

Seq ID No. 68

ATTCTCAACA TAAAAAACTT TGTGTAATAC TTGTAACGCT AGATCCGGTA GCGATCGAAA GCGAAGCGGC

ACTGCTCTTT AACAATTTAT CAGACAATCT GTGTGGGCAC TCGAAGATAC GGATTCTTAA CGTCGCAAGA

CGAAAAATGA ATACCAAGTC TCAAGAGTGA ACACGTAATT CATTACGAAG TTTAATTCTT TGAGCGTCAA

ACTTTTAAAT TGAAGAGTTT GATCATGGCT CAGATTGAAC GCTGGCGGCA GGCCTAACAC ATGCAAGTCG

AACGGTAACA GGAAGAAGCT TGCTTCTTTG CTGACGAGTG GCGGACGGGT GAGTAATGTC TGGGAAACTG

CCTGATGGAG GGGGATAACT ACTGGAAACG GTAGCTAATA CCGCATAACG TCGCAAGACC AAAGAGGGGG

ACCTTCGGGC CTCTTGCCAT CGGATGTGCC CAGATGGGAT TAGCTAGTAG GTGGGGTAAC GGCTCACCTA

GGCGACGATC CCTAGCTGGT CTGAGAGGAT GACCAGCCAC ACTGGAACTG AGACACGGTC CAGACTCCTA

CGGGAGGCAG CAGTGGGGAA TATTGCACAA TGGGCGCAAG CCTGATGCAG CCATGCCGCG TGTATGAAGA

AGGCCTTCGG GTTGTAAAGT ACTTTCAGCG GGGAGGAAGG GAGTAAAGTT AATACCTTTG CTCATTGACG

TTACCCGCAG AAGAAGCACC GGCTAACTCC GTGCCAGCAG CCGCGGTAAT ACGGAGGGTG CAAGCGTTAA

TCGGAATTAC TGGGCGTAAA GCGCACGCAG GCGGTTTGTT AAGTCAGATG TGAAATCCCC GGGCTCAACC

TGGGAACTGC ATCTGATACT GGCAAGCTTG AGTCTCGTAG AGGGGGGTAG AATTCCAGGT GTAGCGGTGA

AATGCGTAGA GATCTGGAGG AATACCGGTG GCGAAGGCGG CCCCCTGGAC GAAGACTGAC GCTCAGGTGC

GAAAGCGTGG GGAGCAAACA GGATTAGATA CCCTGGTAGT CCACGCCGTA AACGATGTCG ACTTGGAGGT

```
TGTGCCCTTG AGGCGTGGCT TCCGGAGCTA ACGCGTTAAG TCGACCGCCT GGGGAGTACG GCCGCAAGGT

TAAAACTCAA ATGAATTGAC GGGGGCCCGC ACAAGCGGTG GAGCATGTGG TTTAATTCGA TGCAACGCGA

AGAACCTTAC CTGGTCTTGA CATCCACGGA AGTTTTCAGA GATGAGAATG TGCCTTCGGG AACCGTGAGA

CAGGTGCTGC ATGGCTGTCG TCAGCTCGTG TTGTGAAATG TTGGGTTAAG TCCCGCAACG AGCGCAACCC

TTATCCTTTG TTGCCAGCGG TCCGGCCGGG AACTCAAAGG AGACTGCCAG TGATAAACTG GAGGAAGGTG

GGGATGACGT CAAGTCATCA TGGCCCTTAC GACCAGGGCT ACACACGTGC TACAATGGCG CATACAAAGA

GAAGCGACCT CGCGAGAGCA AGCGGACCTC ATAAAGTGCG TCGTAGTCCG GATTGGAGTC TGCAACTCGA

CTCCATGAAG TCGGAATCGC TAGTAATCGT GGATCAGAAT GCCACGGTGA ATACGTTCCC GGGCCTTGTA

CACACCGCCC GTCACACCAT GGGAGTGGGT TGCAAAAGAA GTAGGTAGCT TAACCTTCGG GAGGGCGCTT

ACCACTTTGT GATTCATGAC TGGGGTGAAG TCGTAACAAG GTAACCGTAG GGGAACCTGC GGTTGGATCA

TGGGGTACCT TAAAGAAGCG TACTTTGTAG TGCTCACACA GATTGTCTGA TA
```

A nearly complete lack of fluorescence by *E. coli* DH5α cells transformed with pSH3-KF was observed (FIG. 2B) as determined by plate reader fluorescence assays (see cell density and fluorescence assays section, above, for experimental details). However, fluorescence of *E. coli* DH5α cells transformed with pSH3-KF could be recovered in a dose-dependent manner by addition of various concentrations of anhydrotetracycline (ATC), which binds to TetR and causes its dissociation from PLtetO-1 thereby relieving repression of transcription (FIG. 16).

2.4. Ribosome Inhibition Assays Using pSH Series Plasmids in *E. coli* SH386 and SH424.

2.4.1. Ribosome Inhibition Assay of Kanamycin in *E. coli* SH391.

The ability of *E. coli* SH386 cells transformed with pSH3-KF (referred to as *E. coli* SH391) to detect ribosome inhibition by kanamycin was tested. *E. coli* SH391 cells were grown in the presence of various concentrations of kanamycin ranging from 0-500 µM and analyzed by fluorescence assay (see Section 1.6 for experimental details). *E. coli* SH391 displayed strong fluorescence in the absence of kanamycin and only a modest (~50%) increase in fluorescence when kanamycin was added (FIG. 3). This result led to construction and testing of plasmids pSH4-KF-pSH14-KF in *E. coli* SH386.

2.4.2. Construction and Testing of pSH4-KF-pSH14-KF in *E. coli* SH386.

To attempt to overcome the low sensitivity to kanamycin and high background fluorescence imparted by pSH3-KF in *E. coli* SH386 (FIG. 3), a series of eleven pSH3-KF variants were constructed in which the strengths of the two promoters controlling expression of tetR and O-16S rRNA were combinatorially altered using synthetic constitutive promoters with characterized strengths (J. Christopher Anderson, unpublished,). In addition to the original medium strength synthetic promoter BBa_J23106 controlling tetR expression, strong promoter BBa_J23100 and weak promoter BBa_J23115 were selected for use with tetR. In addition to the original lpp promoter controlling O-16S rRNA expression, strong promoter BBa_J23100, medium strength promoter BBa_J23108, and weak strength promoter BBa_J23114 were selected for use with O-16S rRNA. Promoter information is provided in Table 9.

TABLE 9

| Name | Sequence | Strength |
| --- | --- | --- |
| BBa_J23100 | TTGACGGCTAGCTCAGTCCTAGGTAC<br>AGTGCTAGC Seq ID No. 69 | Strong (1.0) |
| BBa_J23106 | TTTACGGCTAGCTCAGTCCTAGGTAT<br>AGTGCTAGC Seq ID No. 70 | Medium (0.47) |
| BBa_J23115 | TTTATAGCTAGCTCAGCCCTTGGTAC<br>AATGCTAGC Seq ID No. 71 | Weak (0.15) |
| BBa_J23108 | CTGACAGCTAGCTCAGTCCTAGGTAT<br>AATGCTAGC Seq ID No. 72 | Medium (0.51) |
| BBa_J23114 | TTTATGGCTAGCTCAGTCCTAGGTAC<br>AATGCTAGC Seq ID No. 73 | Weak (0.10) |
| IPP | TTCTCAACATAAAAAACTTTGTGTAA<br>TACT Seq ID No. 74 | |

Figure 17:
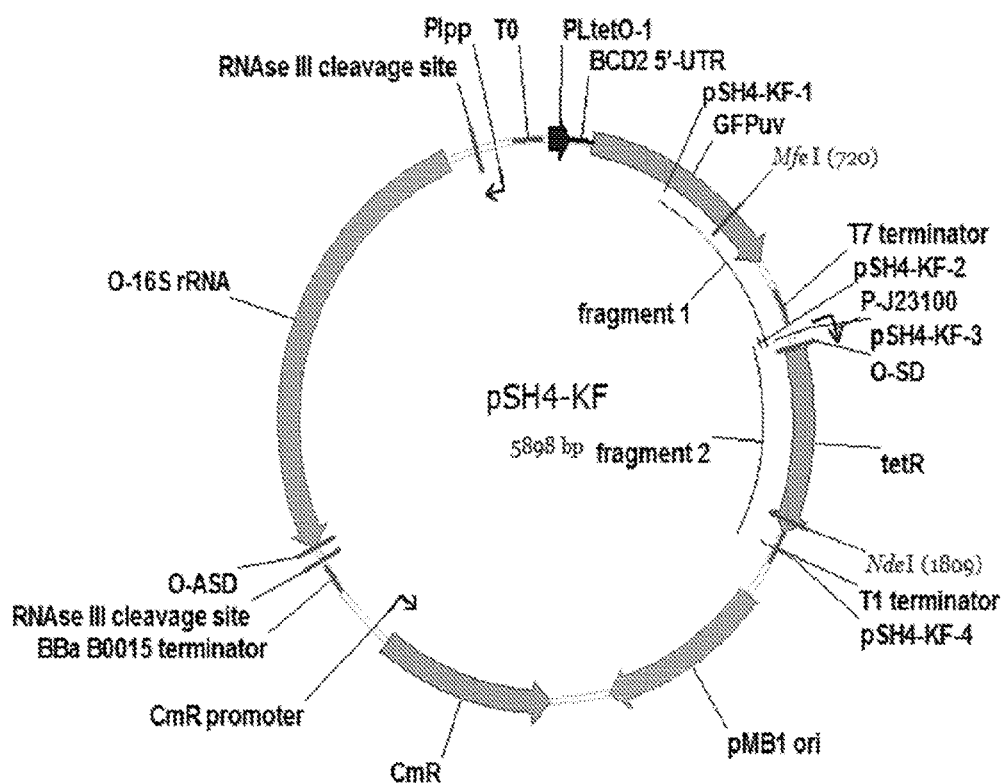
FIG. 17. Plasmid map of pSH4-KF.

First, plasmids pSH4-KF (FIG. 17) and pSH5-KF were constructed, in which the BBa_J23106 promoter controlling expression of tetR was replaced with strong promoter BBa_J23100 and a weak promoter BBa_J23115, respectively. Promoter replacement was accomplished by overlap extension PCR of two fragments amplified from pSH3-KF whose junction encompassed each promoter to be inserted, digestion of both the resulting PCR product and pSH3-KF with unique restriction sites MfeI and NdeI, and ligation of the PCR product into the vector. For construction of pSH4-KF, primer pSH4-KF-1 and mutagenic primer pSH4-KF-2 were used to amplify fragment 1; and mutagenic primer pSH4-KF-3 and primer pSH4-KF-4 were used to amplify fragment 2. For construction of pSH5-KF, primer pSH4-KF-1 and mutagenic primer pSH5-KF-2 were used to amplify fragment 1; and mutagenic primer pSH5-KF-3 and primer pSH4-KF-4 were used to amplify fragment 2. Plasmids pSH4-KF and pSH5-KF were verified by sequencing the cloned region. Primer information is provided in Table 10. The priming region of each primer is underlined.

To construct the remaining nine plasmid variants bearing strong (pSH6-KF, pSH9-KF, pSH12-KF), medium (pSH7-KF, pSH10-KF, pSH13-KF), and weak (pSH8-KF, pSH11-KF, pSH14-KF) strength promoters controlling expression of O-16S, a similar overlap extension PCR strategy was used. Two fragments amplified from pSH3-KF whose junction encompassed each promoter to be inserted were joined by overlap extension PCR. The PCR product bearing strong promoter BBa_J23100 was constructed using primer pSH6-KF-1 and mutagenic primer pSH6-KF-2 to amplify fragment 1; and mutagenic primer pSH6-KF-3 and primer pSH6-KF-4 to amplify fragment 2. The PCR product bearing medium promoter BBa_J23108 was constructed using primer pSH6-KF-1 and mutagenic primer pSH7-KF-2 to amplify fragment 1; and mutagenic primer pSH7-KF-3 and primer pSH6-KF-4 to amplify fragment 2. The PCR product bearing weak promoter BBa_J23114 was constructed using primer pSH6-KF-1 and mutagenic primer pSH8-KF-2 to amplify fragment 1; and mutagenic primer pSH8-KF-3 and primer pSH6-KF-4 to amplify fragment 2. Each of the resulting three PCR products was digested with unique restriction enzymes PstI and SpeI and ligated into each pSH3-KF, pSH4-KF, and pSH5-KF digested with the same enzymes to generate the nine final constructs pSH6-KF through pSH14-KF. All nine plasmids were verified by sequencing the cloned region. Primer information is provided in Table 10. The priming region of each primer is underlined. Regions of the mutagenic primers containing promoter regions are show in bold.

TABLE 10

| primer name | sequence (5'-3') | amplicon size (bp) | template |
| --- | --- | --- | --- |
| pSH4-KF-1 | ACGGGAACTACAAGACGCGTGCTG Seq ID No. 75 | 725 | pSH3-KF |
| pSH4-KF-2 | GCTAGCACTGTACCTAGGACTGAG CTAGCCGTCAACCGGGCCTCTTGC GGG Seq ID No. 76 | | |
| pSH4-KF-3 | CAGTCCTAGGTACAGTGCTAGCCC AGCCAGAG Seq ID No. 77 | 769 | pSH3-KF |
| pSH4-KF-4 | CCTACTCAGGAGAGCGTTCACCG Seq ID No. 78 | | |
| pSH5-KF-2 | GCTAGCATTGTACCTAGGACTGAG CTAGCTATAAACCGGGCCTCTTGC GGG (used with pSH4-KF-1) Seq ID No. 79 | 725 | pSH3-KF |
| pSH5-KF-3 | CAGTCCTAGGTACAATGCTAGCCC AGCCAGAG (used with pSH4-KF-4) Seq ID No. 80 | 769 | pSH3-KF |
| pSH6-KF-1 | GTGACTCTAGTAGAGAGCGTTCAC CGAC Seq ID No. 81 | 1926 | pSH3-KF |
| pSH6-KF-2 | TTGACGGCTAGCTCAGTCCTAGGT ACAGTGCTAGCTACTTGTAACGCT AGATCCGG Seq ID No. 82 | | |
| pSH6-KF-3 | AGGACTGAGCTAGCCGTCAATCGT GGCCCTGCATGCAC Seq ID No. 83 | 375 | pSH3-KF |
| pSH6-KF-4 | GGGACAACTCCAGTGAAAAGTTCT TCTCC Seq ID No. 84 | | |
| pSH7-KF-2 | CTGACAGCTAGCTCAGTCCTAGGT ATAATGCTAGCTACTTGTAACGCT AGATCCGG (used with pSH6-KF-1) Seq ID No. 85 | 1926 | pSH3-KF |
| pSH7-KF-3 | AGGACTGAGCTAGCCATAAATCGT GGCCCTGCATGCAC (used with pSH6-KF-4) Seq ID No. 86 | 375 | pSH3-KF |
| pSH8-KF-2 | TTTATGGCTAGCTCAGTCCTAGGT ACAATGCTAGCTACTTGTAACGCT AGATCCGG (used with pSH6-KF-1) Seq ID No. 87 | 1926 | pSH3-KF |
| pSH8-KF-3 | AGGACTGAGCTAGCCATAAATCGT GGCCCTGCATGCAC (used with pSH6-KF-4) Seq ID No. 88 | 375 | pSH3-KF |

Figure 18:
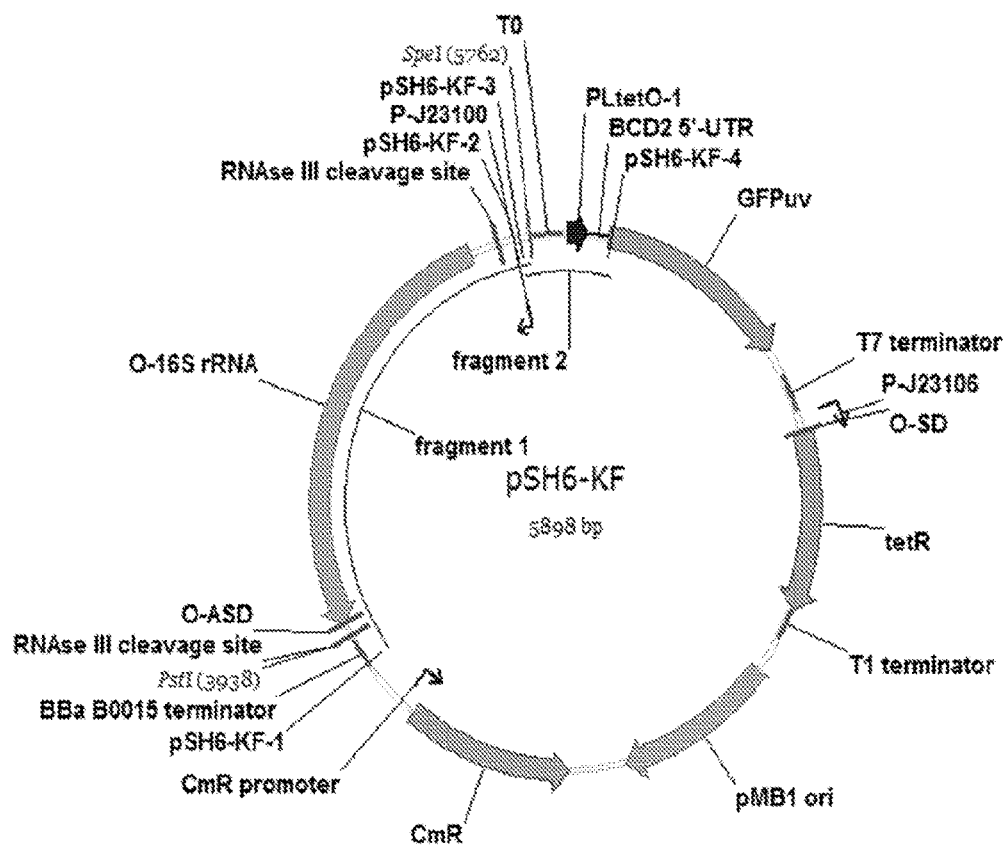
FIG. 18. Plasmid map of pSH6-KF.

Plasmid maps of pSH4-KF (FIG. 17) and pSH6-KF (FIG. 18) are shown as examples. Summaries of the names, sequences, and strengths (as measured by J. Christopher Anderson, unpublished) of the promoters used and of the tetR and O-16S promoters found in each plasmid are summarized in Table 9 and Table 11.

TABLE 11

| | tetR | | O-16S | |
| --- | --- | --- | --- | --- |
| plasmid | promoter | strength | promoter | strength |
| pSH3-KF | BBa_J23106 | Medium (0.47) | lpp | ND |
| pSH4-KF | BBa_J23100 | Strong (1.0) | lpp | ND |
| pSH5-KF | BBa_J23115 | Weak (0.15) | lpp | ND |
| pSH6-KF | BBa_J23106 | Medium (0.47) | BBa_J23100 | Strong (1.0) |
| pSH7-KF | BBa_J23106 | Medium (0.47) | BBa_J23108 | Medium (0.51) |
| pSH8-KF | BBa_J23106 | Medium (0.47) | BBa_J23114 | Weak (0.10) |
| pSH9-KF | BBa_J23100 | Strong (1.0) | BBa_J23100 | Strong (1.0) |
| pSH10-KF | BBa_J23100 | Strong (1.0) | BBa_J23108 | Medium (0.51) |
| pSH11-KF | BBa_J23100 | Strong (1.0) | BBa_J23114 | Weak (0.10) |
| pSH12-KF | BBa_J23115 | Weak (0.15) | BBa_J23100 | Strong (1.0) |
| pSH13-KF | BBa_J23115 | Weak (0.15) | BBa_J23108 | Medium (0.51) |
| pSH14-KF | BBa_J23115 | Weak (0.15) | BBa_J23114 | Weak (0.10) |

*E. coli* SH386 cells transformed with pSH4-KF-pSH14-KF displayed a range of kanamycin concentration-dependent fluorescent phenotypes as determined by plate reader fluorescence assays (see cell density and fluorescence assays section, above, for experimental details). *E. coli* SH386 cells transformed with pSH6-KF (referred to as *E. coli* SH391) displayed the most favorable properties: essentially no background fluorescence in the absence of kanamycin, and a robust dose-dependent increase in fluorescence in response to kanamycin (FIG. 3). Thus, *E. coli* SH391 was selected for subsequent experiments. Interestingly, the results are consistent with the lpp promoter being the weakest of the six promoters tested. The full fluorescence quantification data are shown in FIG. 19.

2.4.3. Ribosome Inhibition Assays of Aminoglycosides in *E. coli* SH399 and SH431.

*E. coli* SH399, which harbors detection plasmid pSH6-KF, was used to conduct ribosome inhibition assays using a range of concentrations of seven structurally diverse aminoglycosides—kanamycin, apramycin, neomycin, paromomycin, gentamicin, geneticin (G418), and hygromycin—over a range of nineteen drug concentrations. Dose-dependent fluorescence responses by *E. coli* SH399 was observed when treated with five of these compounds as determined by plate reader fluorescence assays (see section 1.6 for experimental details). (FIG. 4A and FIG. 20).

To extend the approach to a system with a different aminoglycoside resistance mutation, prrnC-sacB was replaced with pRRSH2-U1406A (see Section 2.2.2 for vector construction) in *E. coli* SQ380 (*E. coli* SH424), which was then transformed with pSH6-KF, resulting in the detection strain *E. coli* SH431. *E. coli* SH431 was used to conduct ribosome inhibition assays identical to those performed with *E. coli* SH399. Dose-dependent fluorescence responses by *E. coli* SH431 were observed when treated with four of these compounds as determined by plate reader fluorescence assays (see section 1.6 for experimental details), including two to which *E. coli* SH399 was not resistant and therefore could not produce a response. (FIG. 4B and FIG. 20).

As a control to check for innate resistance on the part of *E. coli* SQ380 to any of the aminoglycosides tested, *E. coli* SH434 was constructed, which contains pRRSH2 (wild-type 16S rRNA, see Section 2.2.2 for vector construction and Section 2.2.3 for functional testing), and examined its growth in the presence of a range of concentrations of each aminoglycoside. *E. coli* SH434 did not display innate resistance to any of the compounds except moderately to hygromycin. However, this did not prevent detection of ribosome inhibition by hygromycin in SH431.

The complete disclosure of all patents, patent applications, and publications, and electronically available material (including, for instance, nucleotide sequence submissions in, e.g., GenBank and RefSeq, and amino acid sequence submissions in, e.g., SwissProt, PIR, PRF, PDB, and translations from annotated coding regions in GenBank and RefSeq) cited herein are incorporated by reference in their entirety. In the event that any inconsistency exists between the disclosure of the present application and the disclosure(s) of any document incorporated herein by reference, the disclosure of the present application shall govern. The foregoing detailed description and examples have been given for clarity of understanding only. No unnecessary limitations are to be understood therefrom. The invention is not limited to the exact details shown and described, for variations obvious to one skilled in the art will be included within the invention defined by the claims.

Unless otherwise indicated, all numbers expressing quantities of components, molecular weights, and so forth used in the specification and claims are to be understood as being modified in all instances by the term "about." Accordingly, unless otherwise indicated to the contrary, the numerical parameters set forth in the specification and claims are approximations that may vary depending upon the desired properties sought to be obtained by the present invention. At the very least, and not as an attempt to limit the doctrine of equivalents to the scope of the claims, each numerical parameter should at least be construed in light of the number of reported significant digits and by applying ordinary rounding techniques.

Notwithstanding that the numerical ranges and parameters setting forth the broad scope of the invention are approximations, the numerical values set forth in the specific examples are reported as precisely as possible. All numerical values, however, inherently contain a range necessarily resulting from the standard deviation found in their respective testing measurements.

All headings are for the convenience of the reader and should not be used to limit the meaning of the text that follows the heading, unless so specified.

What is claimed is:

1. A method of measuring ribosome inhibition, the method comprising:
   providing a genetically-modified cell comprising:
   an aminoglycoside-sensitive orthogonal 16S rRNA (O-16S) coding region bearing a mutated anti-Shine-Dalgarno (O-ASD) sequence;
   a repressor/operator pair that comprises:
   a coding region that encodes a transcriptional regulator and having an orthogonal SD (O-SD) sequence complementary to the 16S rRNA O-ASD sequence; and
   an operator sequence repressable by the transcriptional regulator; and
   a polynucleotide encoding a detectable reporter operably linked to the operator sequence repressable by the transcriptional regulator;
   contacting the cell with a test compound; and
   detecting a signal produced by the reporter, wherein intensity of the signal indicates a dose dependent degree of ribosome inhibition.

2. The method of claim 1, wherein the transcriptional regulator comprises TetR.

3. The method of claim 2, wherein the operator sequence repressable by TetR comprises PLtetO-1.

4. The method of claim 1, wherein the detectable reporter comprises a fluorescent polypeptide.

* * * * *

UNITED STATES PATENT AND TRADEMARK OFFICE
CERTIFICATE OF CORRECTION

PATENT NO. : 10,365,269 B2  
APPLICATION NO. : 15/577809  
DATED : July 30, 2019  
INVENTOR(S) : Charles Melancon and Shijie Huang Page 1 of 1

It is certified that error appears in the above-identified patent and that said Letters Patent is hereby corrected as shown below:

On the Title Page

Item (71) Applicant: please delete "Charles Melancon, Albuquerque, NM (US); Shijie Huang, Albuquerque, NM (US)"

Signed and Sealed this  
First Day of October, 2019

Andrei Iancu  
*Director of the United States Patent and Trademark Office*